United States Patent
Kriesel et al.

(12)
(10) Patent No.: US 6,416,495 B1
(45) Date of Patent: Jul. 9, 2002

(54) IMPLANTABLE FLUID DELIVERY DEVICE FOR BASAL AND BOLUS DELIVERY OF MEDICINAL FLUIDS

(75) Inventors: Marshall S. Kriesel, Saint Paul; Thomas N. Thompson, Richfield, both of MN (US)

(73) Assignee: Science Incorporated, Burnsville, MN (US)

(*) Notice: Subject to any disclaimer, the term of this patent is extended or adjusted under 35 U.S.C. 154(b) by 20 days.

(21) Appl. No.: 09/686,650

(22) Filed: Oct. 10, 2000

(51) Int. Cl.[7] .................. A61M 37/00; A61M 5/00; A61K 9/22
(52) U.S. Cl. .................. 604/132; 604/891.1; 604/246
(58) Field of Search .................. 604/19, 20, 93.01, 604/131–133, 153, 246, 82, 83, 85, 890.1, 891.1; 128/899, DIG. 12

(56) References Cited

U.S. PATENT DOCUMENTS 5,779,676 A * 7/1998 Kriesel et al. .............. 604/132
6,117,296 A * 9/2000 Thomson .................. 204/607
6,287,294 B1 * 9/2001 Lemelson .................. 604/132

* cited by examiner

Primary Examiner—Brian L. Casler
Assistant Examiner—Michael J Hayes
(74) Attorney, Agent, or Firm—Schwegman, Lundberg, Woessner & Kluth, P.A.

(57) ABSTRACT

An implantable fluid delivery apparatus for infusing medicinal fluids into a patient that includes a novel basal delivery system that includes a heat responsive polymer gel material which upon being heated by heater foil uniquely functions as an internal energy source for expelling basal doses of medicinal fluids from the device. The apparatus also includes a bolus delivery system that includes a magnetically responsive polymer gel which, upon being stimulated by an electro-magnet will delivery precise bolus doses of medicinal fluids to the patient.

33 Claims, 26 Drawing Sheets

IMPLANTABLE FLUID DELIVERY DEVICE FOR BASAL AND BOLUS DELIVERY OF MEDICINAL FLUIDS

BACKGROUND OF THE INVENTION

FIELD OF THE INVENTION

The present invention relates generally to fluid delivery devices. More particularly, the invention concerns an improved apparatus for delivery of basal and bolus doses of medicinal fluid to a patient that includes internal thermo- and magnetically-responsive energy sources for controllably expelling the fluid from the apparatus.

DISCUSSION OF THE INVENTION

The oral route is the most frequent route of drug administration. Oral administration is relatively easy for most patients and rarely causes physical discomfort. However, many medicinal agents require a parenteral route of administration thus bypassing the digestive system and precluding degradation by the catalytic enzymes in the digestive tract and the liver. The use of more potent medications at elevated concentrations has also increased the need for accuracy in controlling the delivery of such drugs. The delivery device, while not an active pharmacologic agent, may enhance the activity of the drug by medicating its therapeutic effectiveness. Certain classes of new pharmacologic agents posses a very narrow range of therapeutic effectiveness, for instance, too small a dose results in no effect, which to great a dose results in toxic reaction.

In the past, prolonged infusion of fluids has generally been accomplished using gravity flow means coupled with electronic based controls and typically involve the use of intravenous administration sets and the familiar bottle or solution bag suspended above the patient. Such methods are cumbersome, imprecise and, generally non-ambulatory requiring bed confinement of the patient. Periodic monitoring of the apparatus by the nurse or doctor is required to detect malfunctions of the infusion apparatus.

Devices of the character from which liquid is expelled from a relatively thick-walled bladder by internal stresses within the distended bladder have also been suggested for infusion of medicaments. For example, such bladder, or "balloon" type devices, are described in U.S. Pat. No. 3,469,578, issued to Bierman and in U.S. Pat. No. 4,318,400 issued to Perry.

A family of highly unique fluid delivery devices has been developed by the present inventor. These novel devices make use of recently developed elastomeric films, expandable foams and similar materials, which, in cooperation with a base, define a fluid chamber that contains the fluid to be dispensed. The elastomeric film membrane or the expandable member controllably forces fluid within the chamber into outlet fluid flow channels provided in the device. Elastomeric film membrane devices are described in detail in U.S. Pat. No. 5,205,820 issued to the present inventor. U.S. Pat. No. 5,468,226, also issued to the present inventor, describes various types of expandable cellular elastomers and elastomeric foams used as the energy source of the fluid delivery device for expelling fluid from various physical forms of the fluid delivery device. Because of the pertinence of U.S. Pat. Nos. 5,205,820 and 5,468,226, these patents are hereby incorporated herein by reference in their entirety as though fully set forth herein. U.S. Pat. No. 5,961,492 entitled Fluid Delivery Device with Temperature Controlled Energy Source, in which the present inventor is named as a co-inventor is also incorporated by reference as though fully set forth herein. Another patent issued to the present invention, namely U.S. Pat. No. 5,776,103, describes a fluid delivery device with a bolus injection site.

The apparatus of the present invention, comprises a unique, implantable unit that makes use of novel thermo- and electro-stimulated gel materials as energy sources for delivery to the patient of both basal and bolus doses of medicinal fluids. By way of example, the apparatus of the invention can be used for both the continuous basal infusion of a variety of beneficial agents such as heparin, morphine, insulin and like agents as well as for the bolus delivery of such fluids as may be required. With this type of construction, if, for example, the apparatus is being used for basal delivery of insulin over an extended period of time, should a bolus delivery of medication be required to manage an anticipated increase in blood sugar, such a bolus delivery can be quickly and easily accomplished thereby eliminating the need for a direct subdermal injection at an alternate site on the individual's body. In similar manner, the implantable device of the invention can be used to precisely administer both basal and bolus delivery of a number of types of beneficial agents to the patient.

SUMMARY OF THE INVENTION

It is an object of the present invention to provide a technically advanced, fluid delivery apparatus for both basal and bolus infusion of medicinal fluids into a patient. More particularly, it is an object of the invention to provide an apparatus of such a character that is implantable into the patient's body and includes novel light, thermal, magnetically and electrically stimulated polymer gel materials which uniquely function as internal energy sources for controllably expelling the medicinal fluids from the device.

Another object of the invention is to provide an implantable fluid delivery apparatus that can be used for the precise infusion of various pharmaceutical fluids into the patient at controlled rates over extended periods of time.

Another object of the invention is to provide an apparatus of the aforementioned character that is very small, is of a simple construction and yet is highly reliable in operation.

Another object of the invention is to provide an apparatus that embodies as one of its stored energy sources, a soft, pliable, semi-solid, thermo-responsive mass that is controllably heated by an external stimulus in a manner to controllably expel basal doses of medication to the patient.

Another object of the invention is to provide an apparatus as describe in the preceding paragraph in which the heat expandable mass is specifically tailored to provide precise, predictable protocol delivery of the medicinal agent stored within the reservoir of the device.

Another object of the invention is to provide an apparatus that embodies as the other of its stored energy sources, a magnetically responsive mass, such as a ferrogel which is stimulated in a manner to controllably deliver bolus doses of medication to the patient.

Another further object of the invention is to provide an apparatus of the character described in which the thermo- and magnetically responsive stored energy sources can be constructed from various types of polymeric conformable materials such as phase transition gels.

Another object of the invention is to provide an apparatus that embodies as one of its stored energy sources, a soft, pliable, semi-solid mass that is responsive to light in a manner to controllably expel basal doses of medication to the patient.

Another object of the invention is to provide an apparatus as described in the preceding paragraph in which the light stimulated mass is specifically tailored to provide precise, predictable protocol delivery of the medicinal agent stored within the reservoir of the device.

Another object of the invention is to provide an apparatus of the character described in the preceding two paragraphs that embodies as another energy source, an electrically responsive mass, such as a laminate gel construction which is stimulated in a manner to controllably deliver bolus doses of medication to the patient.

Another object of the invention is to provide stored energy sources of the character described in the preceding paragraphs which comprise blends or laminate constructions of phase transition gels that will enable the achievement of multi-rate delivery protocols.

Another object of the invention is to provide an implantable device of the character described that includes fill means for filing the cooperating reservoirs of the device.

Another object of the invention is to provide an implantable fluid delivery device as described in the preceding paragraphs that includes physiological sensor means for sensing physiological changes in the patient's body.

Another object of the invention is to provide an apparatus of the character described which, due to its unique construction, can be manufactured inexpensively in large volume by automated machinery.

Another object of the invention is to provide an implantable fluid delivery device that includes a stored energy source comprising an expandable gel that is stimulated by a heating foil disposed proximate the gel.

Another object of the invention is to provide a device as described in the preceding paragraph which also includes a stored energy source that comprises an expandable ferrogel that is magnetically stimulated to controllably deliver bolus doses of medicament from the device.

Another object of the invention is to provide an implantable fluid delivery device that includes a stored energy source comprising an expandable gel that is stimulated by a light source in the form of a light sheet that is disposed proximate the gel.

Another object of the invention is to provide a device as described in the preceding paragraph which also includes a stored energy source that comprises a laminate gel construction that is electrically stimulated so as to flex in a manner to controllably delivery bolus doses of medicament from the device.

Other objects of the invention will become apparent from the discussion, which follows:

DESCRIPTION OF THE INVENTION

Figure 3:
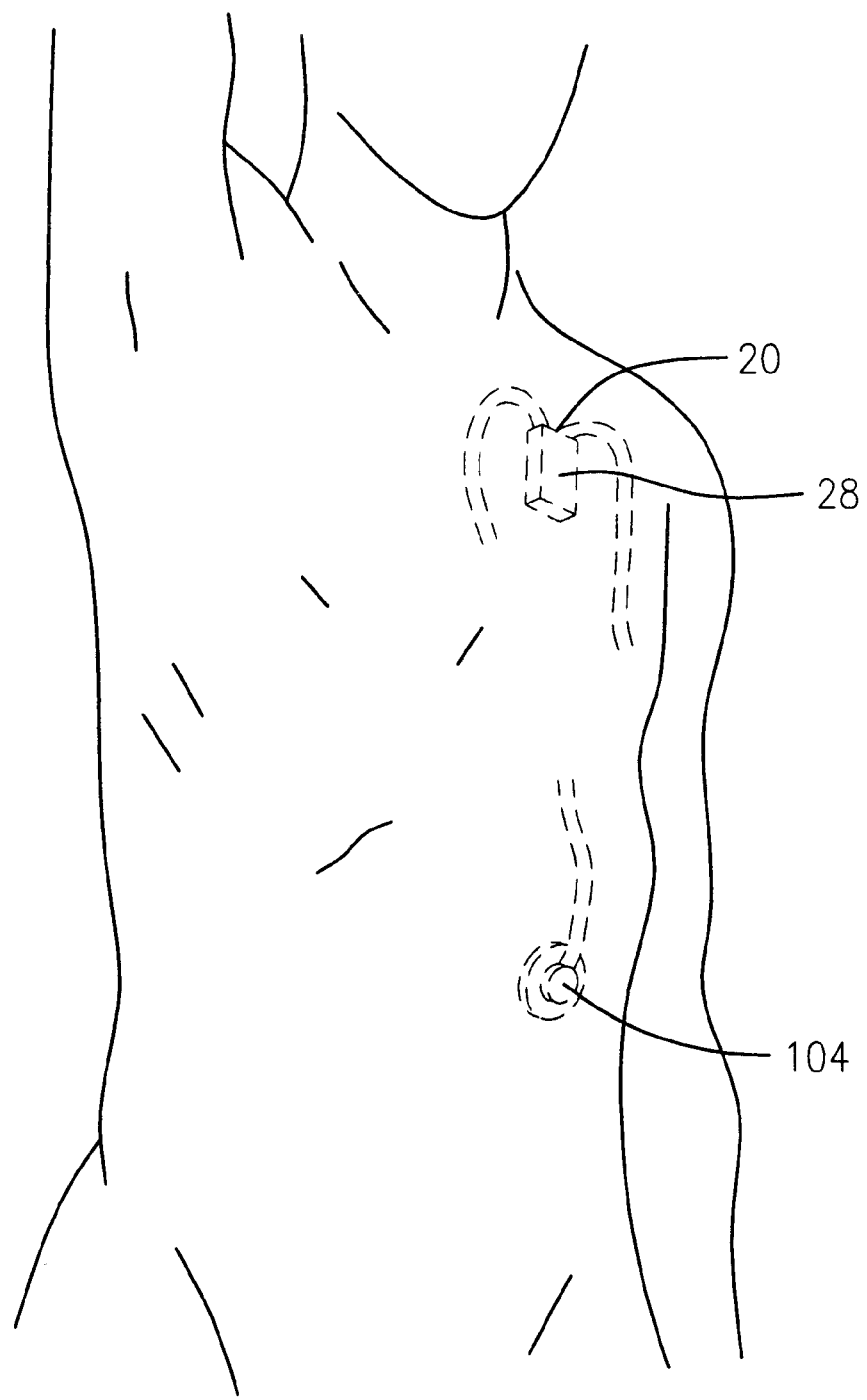
FIG. 3 is a generally perspective, illustrative view showing the delivery device of FIG. 1 implanted within the patient's body.
Figure 4:
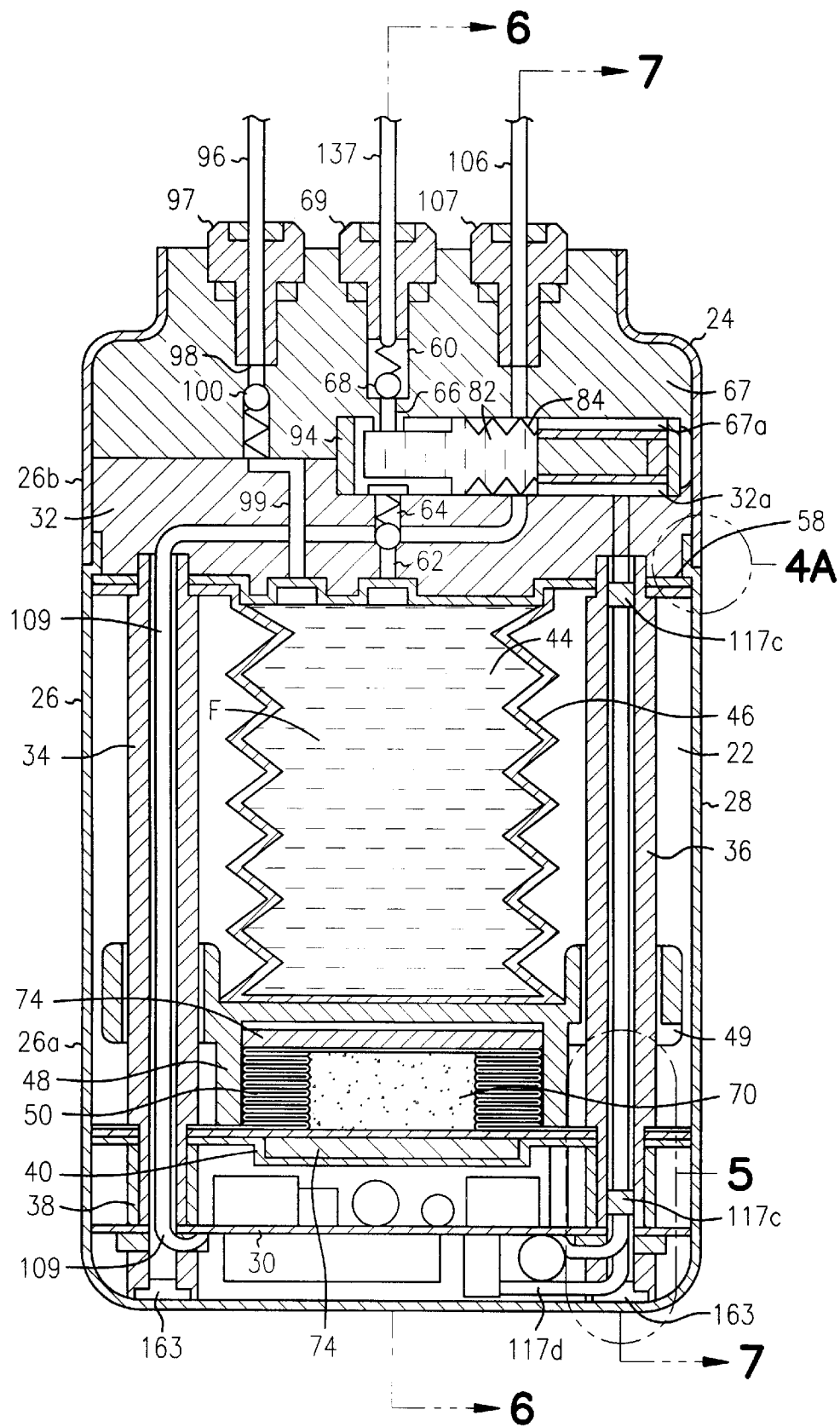
FIG. 4 is a cross-sectional view taken along lines 4—4 of FIG. 2.
Figure 4A:
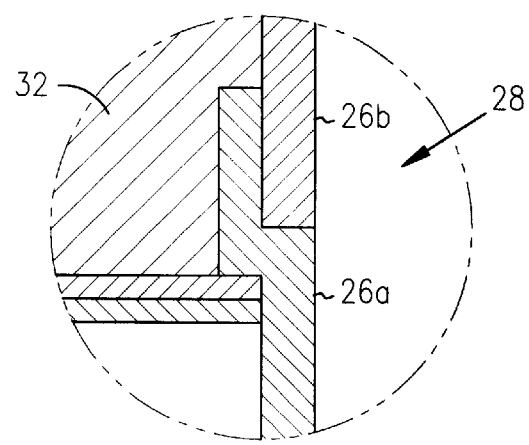
FIG. 4A is an enlarged, cross-sectional view of the area designated as "4A" in FIG. 4.
Figure 9:
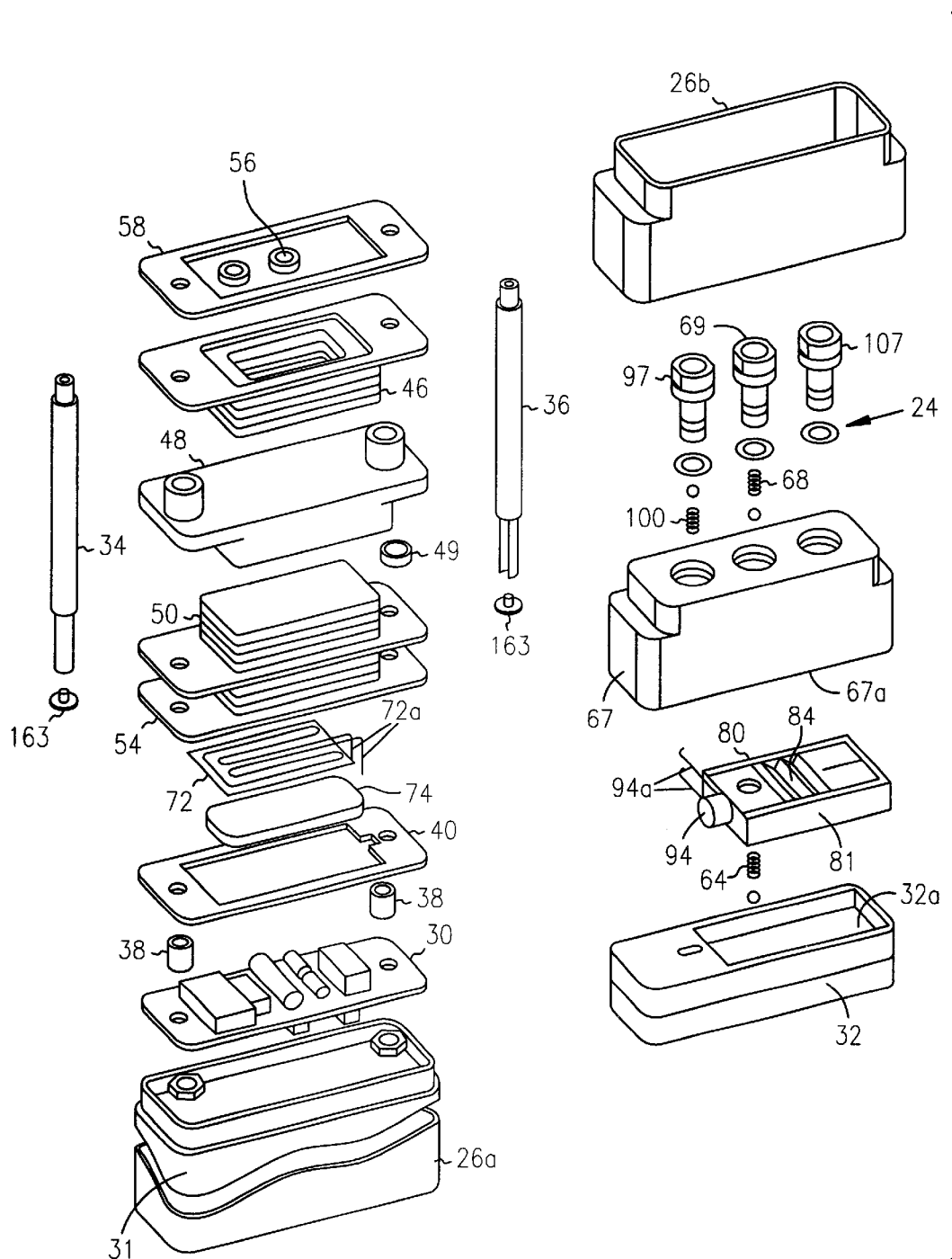
FIG. 9 is a generally perspective, exploded view of the assembly shown in FIG. 4.

Referring to the drawings and particularly to FIGS. 1 through 4, one form of the apparatus of the invention is there shown and generally designated by the numeral 20. As indicated in FIG. 3 of the drawings, this embodiment of the invention, is specially designed to be implanted into the body of the patient. As shown in FIG. 4, the apparatus here comprises a base assembly 22 and a cover assembly 24 that are encapsulated within a thin metal casing 26. As shown in FIGS. 4 and 9, casing 26 comprises a lower portion 26a and an upper portion 26b which are interconnected to form the hermetically sealed housing 28 of the device.

Base assembly 22 here comprises a printed circuit (PC) board 30 which is mounted on a lower case housing 31 (FIG. 9) and is interconnected with a vertically spaced-apart lower fitting block 32 by means of a pair of transversely spaced-apart, threaded support shafts 34 and 36. Spaced apart from PC board 30 by spacers 38 (FIG. 9) is a support plate 40. Mounted on the PC board 30 are the various electronic components of the device, the character of which will later be described. Positioned between plate 40 and fitting block 32 is a first fluid reservoir 44 and the first stored energy means of the invention for expelling fluid from first reservoir 44 at a precise delivery rate.

Figure 6:
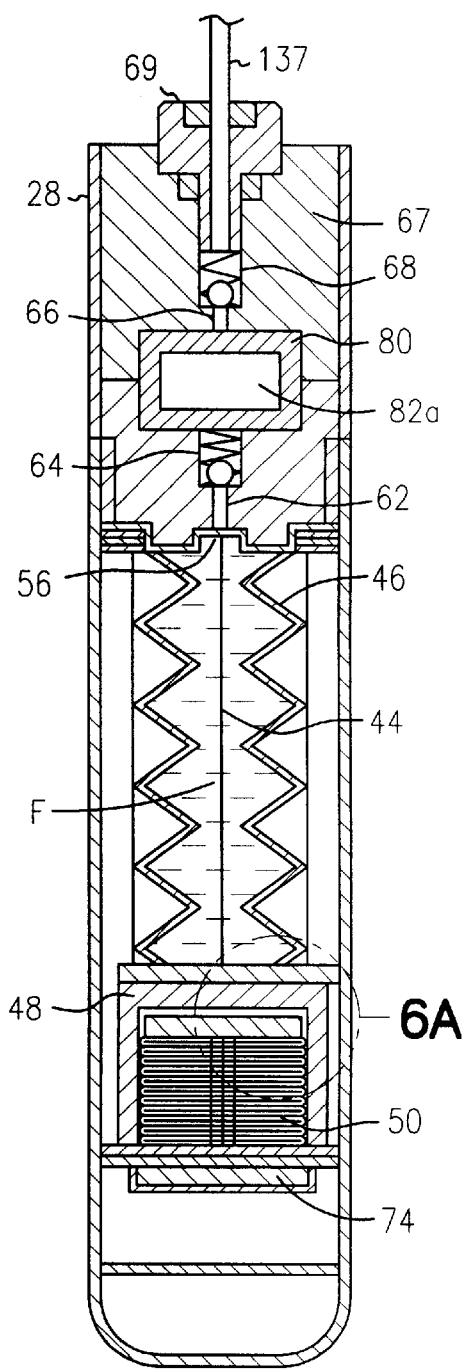
FIG. 6 is a cross-sectional view of lines 6—6 of FIG. 4.
Figure 6A:
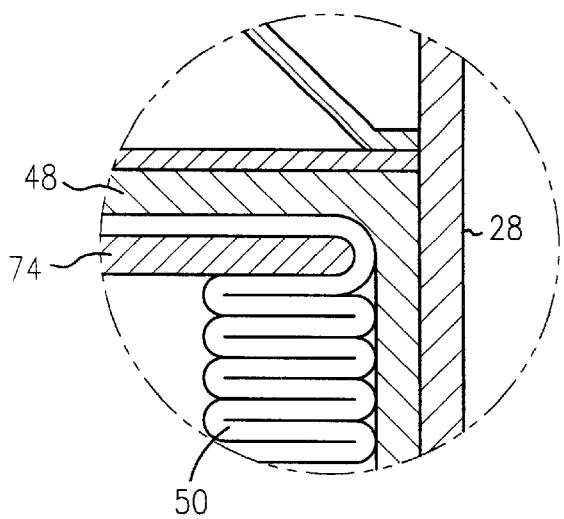
FIG. 6A is an enlarged, cross-sectional view of the area designated as "6A" in FIG. 6.
Figure 10:
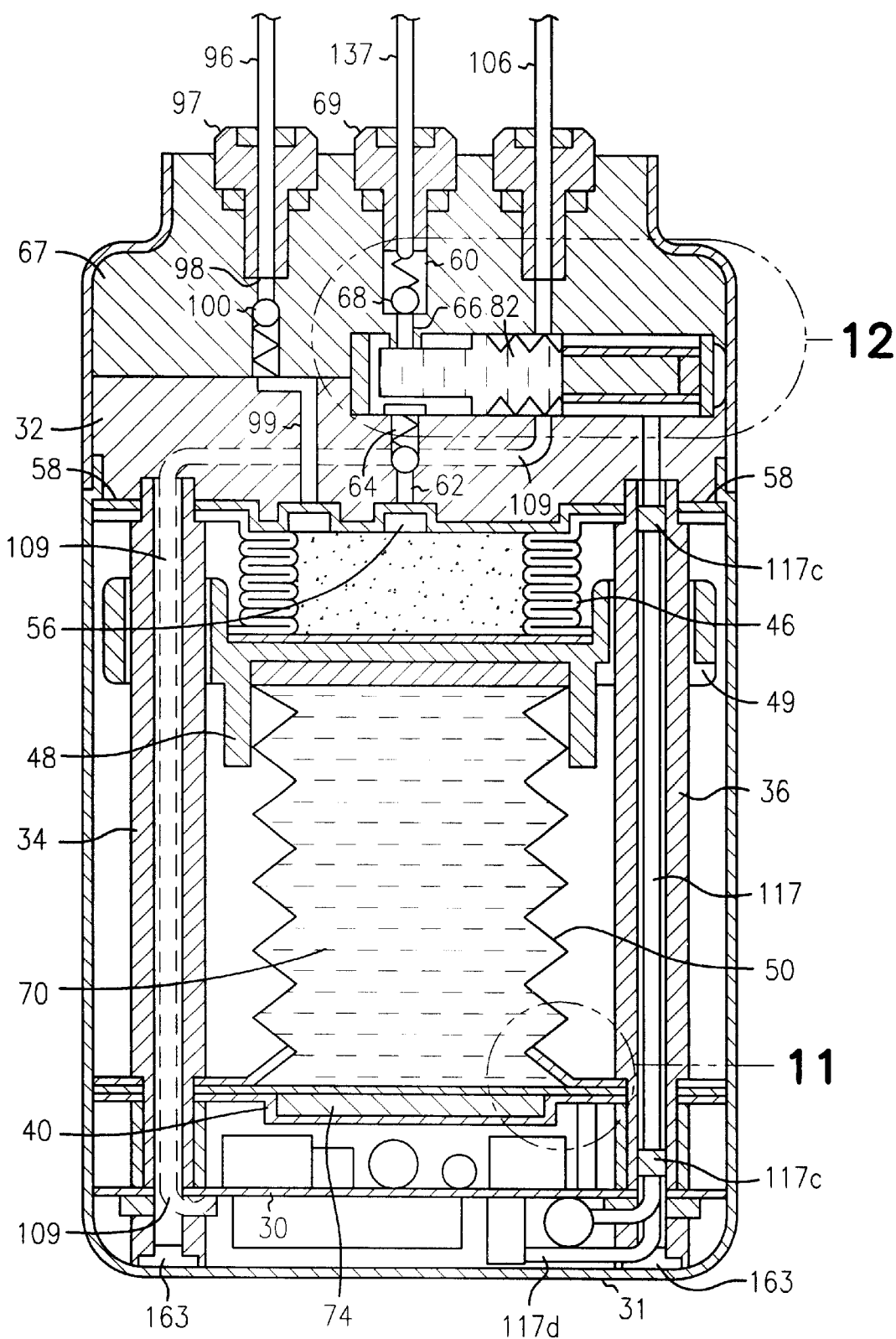
FIG. 10 is a cross-sectional view similar to FIG. 4, but showing the thermo-expandable gel in an expanded configuration following delivery of the medicament to the patient.

First fluid reservoir 44, which contains the medicinal fluid "F" to be delivered to the patient, is defined by an expandable component, here provided as a first expandable bellows 46. In a manner presently to be described, bellows 46 is movable between the expanded configuration shown in FIG. 4 and the collapsed configuration shown in FIG. 10. Disposed between bellows 46 and the first stored energy means is capture housing 48 which is slidably connected to shafts 34 and 36 for movement between a first lowered position shown in FIG. 4 to a second upraised position shown in FIG. 10. Capture housing 48 receives a second expandable component or bellows housing 50 that contains the first stored energy means of the invention (FIG. 6). In a manner presently to be described, bellows housing 50 is expandable from a first collapsed configuration shown in FIGS. 4 and 9 to the expanded configuration shown in FIG. 10. As bellows housing 50 moves into its expanded configuration, capture housing 48 slides upwardly along shafts 34 and 36 into the upraised position shown in FIG. 10. Connected to capture housing 48 is a ring magnet 49 that slides along shaft 36 as the capture housing moves upwardly and downwardly. Magnet 49 comprises a part of the linear displacement measuring means of the invention for precisely determining the amount of fluid remaining within bellows 46. The details of construction and operation of this linear displacement measuring means will later be described.

Located between support plate 40 and a bellows cover plate 54 that closes the lower end of bellows 50 is the important first stimulation means of the invention for stimulating the first stored energy means. The stimulation means functions to stimulate the first stored energy means in a manner to cause it to expand. Expansion of the first stored energy means causes bellows 50 to expand in the manner shown in FIG. 10 and concomitantly causes capture housing 48 to slide upwardly along shafts 34 and 36. This upward movement of capture housing 48 causes bellows 46 to collapse into the configuration shown in FIG. 10. As bellows 46 collapses, the fluid contained therein is forced outwardly of the fluid reservoir through an outlet port 56 formed in a bellows cover 58 which covers bellows 46 in the manner shown in FIGS. 4, 9 and 10. Outlet port 56 communicates with outlet 60 of housing 28 via a first passageway 62, formed in fitting 32, via a check valve 64 mounted within fitting 32, via a second passageway 66 formed in a cover block 67 and via an upper check valve 68 mounted within cover block 67 (FIG. 4). Check valve 68 is held in position within cover block 67 by a threaded fitting 69.

Figure 11:
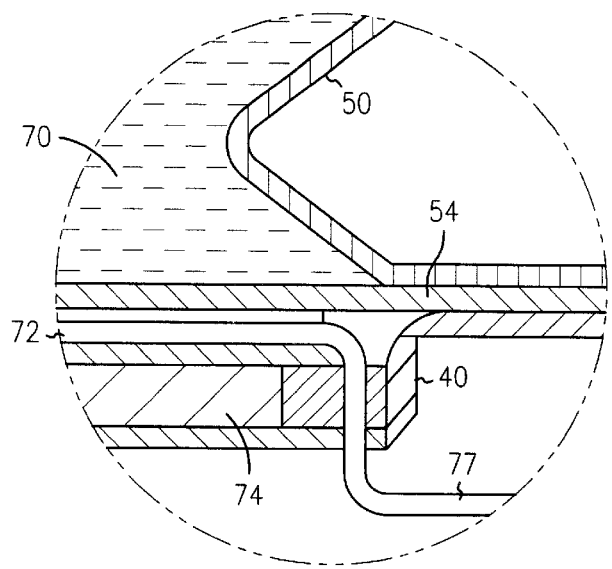
FIG. 11 is an enlarged, cross-sectional view of the area designated as "11 " in FIG. 10.

Considering now the first stimulation means of the invention for stimulating first stored energy source, which here comprises an expandable mass 70, this novel means here comprises a source of heat that includes a heater foil 72 which is carried by a ceramic heat deflector 74 which, in turn, is supported by support plate 40 (FIG. 9). Power is supplied to the heater wires 72a of heater foil 72 (FIG. 11) that are appropriately connected to a source of electricity, the character of which will presently be described. When power is supplied to heater foil 72 via leads 72a, the heater foil will be heated so as to controllably heat expandable mass 70 to a predetermined, substantially constant elevated temperature to enable appropriate expansion thereof. The temperature to which mass 70 is heated is, of course, dependent upon the characteristics of the mass being used.

Considering now, in greater detail, the novel expandable mass 70, this mass is here provided in the form of a polymeric gel. Like most gels, gel or mass 70 is of a semisolid form that can advantageously be handled without external containment under ambient manufacturing conditions. From a technical viewpoint, gels are often characterized as soft solids which reside in a state between a liquid and a solid state. Frequently gels comprise a cross-linked network of long polymer molecules with liquid molecules trapped within the network. Many gels known in the prior art not only are capable of significantly large volume change in response to stimulus (phase-transition gels), but also exhibit physical characteristics that enable them to closely conform to the shape of an adjacent member such as a distendable member.

Polymeric gels best suited for use in constructing the heat expandable mass of the present invention are gels which undergo a change in polymer conformation and in so doing exhibit a large volume change at a given phase-transition condition. Unlike liquids, which exhibit a fixed temperature for state of vaporization to a known volume and with such vaporization point changing as a function of ambient pressure, the phase-transition gels in this invention are multicomponent polymers which can be made to respond with various volume changes to a singular external temperature stimuli to perform useful work.

Advantageously, the difference in volume between the expanded phase of these phase-transition gels and the contracted phase thereof can be orders of magnitude. Examples of suitable phase-transition gels are disclosed in Tanaka et al., U.S. Pat. No. 4,732,930; No. Re-35068 and U.S. Pat. No. 5,403,893. Because of the pertinence of these patents, U.S. Pat. Nos. 4,732,930, 5,403,893 and Patent No. Re-35068 are all hereby incorporated by reference as though fully set forth herein.

While a number of the phase-transition gels described in the Tanaka et al patents can be used to construct the heat expandable stored energy means of the present invention, the ionized acrylamide gel compositions therein described are desirable in many applications because of the quite drastic volume change they exhibit in response to an external stimulus such as the body temperature of the patient. These ionized acrylamide gel compositions comprise a cross-linked, partially ionized polyacrylamide gel wherein between up to 20% of the amide groups are hydrolyzed to carboxyl groups. The gel includes a solvent of a critical concentration at which even a slight change in temperature, pH or salt concentration causes the gel to shrink or swell dramatically. As pointed out by Tanaka et al in the aforementioned patents, the particular critical concentration utilized in the gel composition depends upon the solvent employed, the temperature of the gel and the degree of hydrolysis of the gel. The gel also can contain a positive metal ion such as sodium or magnesium which has the effect of increasing the change in gel volume caused by change of solvent concentration, temperature, pH or, salt concentration.

Another form of phase-transition gel suitable for use in the apparatus of the present invention comprises interpenetrating polymer networks which include a first polymer and a second polymer wherein the second polymer interpenetrates the first polymer. Suitable first and second polymers include polymers which can interact during exposure to a phase-transition condition to thereby cause a significantly large volume change of the gel. Suitable interpenetrating polymer networks can also include more than two polymers. For example, additional polymers can be included in the network which interpenetrate the first and/or second polymers. The nature of these polymers as well as the nature of the interaction between the polymers is discussed in detail in Tanaka, U.S. Pat. No. 5,403,893, and will not here be repeated.

The responsive gels may also be reversibly responsive. For example, when such gels experience certain environmental changes, the entire gel, or a component thereof will undergo a reversible volumetric change which typically involves a shift between two equilibrium states as, for example, expanded and collapsed. This reversible volume change of the entire gel, or a component of the gel may be either continuous or discontinuous. As a general rule, a continuous volume change is marked by a reversible change in volume that occurs over a substantial change in environmental condition. On the other hand, the gel, or a component thereof, may undergo a discontinuous volume change in which the reversible transition from expanded to collapsed states, and back again, typically occurs over a relatively small change in environmental condition. A gel undergoing a continuous phase-transition may have a similar order of magnitude total volume change as a gel undergoing a discontinuous phase-transition.

Typically, volumetric changes in the phase transition gels result from competition between intermolecular forces, usually electrostatic in nature. Such volumetric changes are believed to be driven primarily by four fundamental forces, that is ionic, hydrophobic, hydrogen bonding and van der Waals bonding interactions, either alone or in combination. Changes in temperature most strongly affect hydrophobic interactions and hydrogen bonding.

Of particular interest is the fact that gels consisting of copolymers of positively and negatively charged groups may be formulated so that the volume change is governed by more than one fundamental force. In these gels, polymer segments typically interact with each other through ionic interactions and hydrogen bonding.

By way of summary, gels suitable for use as the stored energy sources of the present invention include various cross-linked polymers and gels which can be synthesized from the polymerization of a monomer and a cross-linking agent. More particularly, suitable gels can be made from any polymer with side groups that can react with a di-or multifunctional cross-linking molecule. However, the simplest system from which gels can be made are polymers with hydroxyl, acid or amine side groups.

By way of non-limiting example, suitable gels for use as the stored energy means may consist, in whole or in part, of polymers made by copolymerization/cross linking of monofunctional and polyfunctional polymerizable vinyl monomers. The monomer may include N, N-disubstituted acrylamides such as N,N-dialkylsubstituted acrylamides, or di-N,N substituted acrylamides where the dissubtitutions form part of a ring, acrylate ethers, alkyl substituted vinyl ethers, glycol ethers, and mixtures thereof.

Exemplary polymeric gel networks thus may contain poly (N,N-dialkylacrylamide), poly(ethyl acrylate) and mixtures thereof, as well as polymers of N-alkylacrylamide (or analogous N-alkylmethacrylamide) derivatives such as N-ethylacrylamide, N-n-propylacrylamide, N-n-propylmethacrylamide, or various acrylate copolymers.

Exemplary cross-linking agents may include ethylene glycol diacrylate (EGDA); di(ethylene glycol)bis(allyl carbonate) ("DEGBAC"); methylenebis(acrylamide) ("bis"); ethylene glycol dimethacrylate ("EGDMA"); magnesium methacrylate ("MgMA$_2$"); and mixtures thereof. Cross-linkers suitable for polymeric precursors may include diglycidyl ether, divinyl sulfone, epichlorohydrin, phosphoryl chloride, trimetaphosphate, trimethylomelamine, polyacrolein, and ceric ion redox systems, although the most preferred of these will not have active hydrogens. The cross-linking agent effects partial cross-linking of the polymer and provides a means to control the gel's mechanical strength, swelling degree, and intensity of volume change trigger by changing the cross-linking density. Cross-linking of linear polymers by chemical reagents is preferred for gels made from biological polymers such as cellulose ethers. Preferred cross-linkers for polysaccharide gels, especially cellulose ethers, are multifunctional carboxylic acids, such as adipic acid (hexanedioic acid: $HOOC(CH_2)_4COOH$), succinic acid ($HOOC(CH_2)_2COOH$), malonic acid (propanedioic acid: $CH_2(COOH)_2$, sebacic acid (decanedioic acid: $HOOC(CH_2)COOH$), glutaric acid (pentanedioic acid: $HOOC(CH_2)_3COOH$), or 1, 10 decanedicarboxylic acid.

Before discussing the operation of the device to provide a precise basal delivery of medicament to the patient through the controlled heating of the heater foil 72, the important bolus delivery means of the invention will next be discussed. This important bolus delivery means of the invention here comprises a delivery assembly 80, which includes a housing 81 that is captured within a cavity 32a formed in fitting block 32 and a cavity 67a formed in cover block 67 (FIGS. 4 and 9). As can best be seen by referring to in FIGS. 12 and 13, delivery assembly 80 includes a second fluid reservoir 82 that is partially defined by a third expandable component shown here as a third expandable bellows 84. Reservoir 82 includes a forward portion 82a that is disposed intermediate of and in communication with the previously identified fluid passageways 62 and 66.

Figure 12:
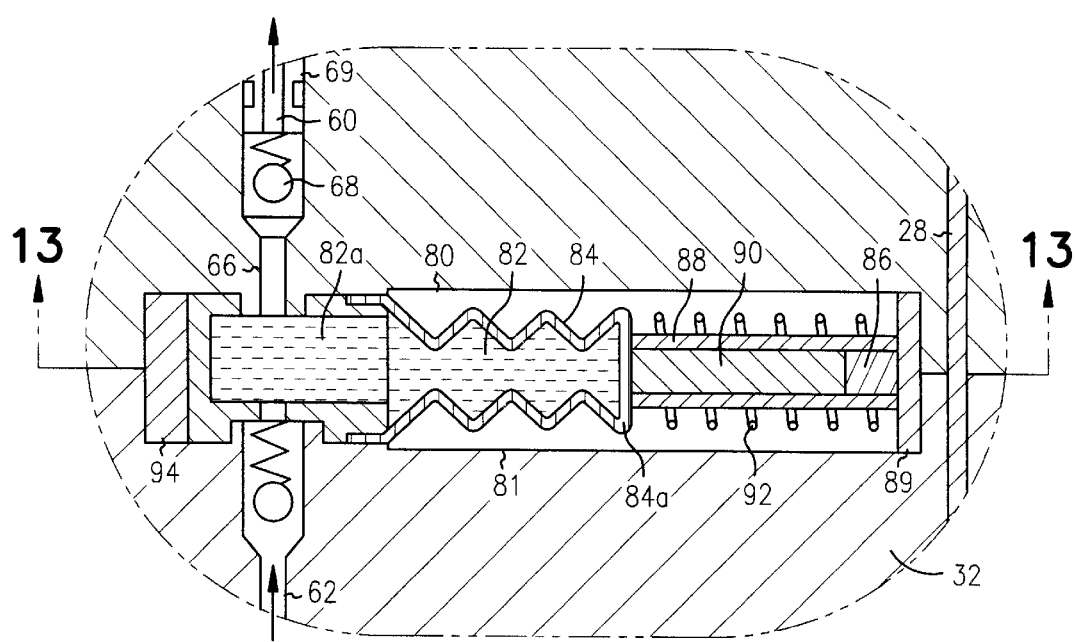
FIG. 12 is an enlarged, cross-sectional view of the area designated as "12" in FIG. 10.
Figure 13:
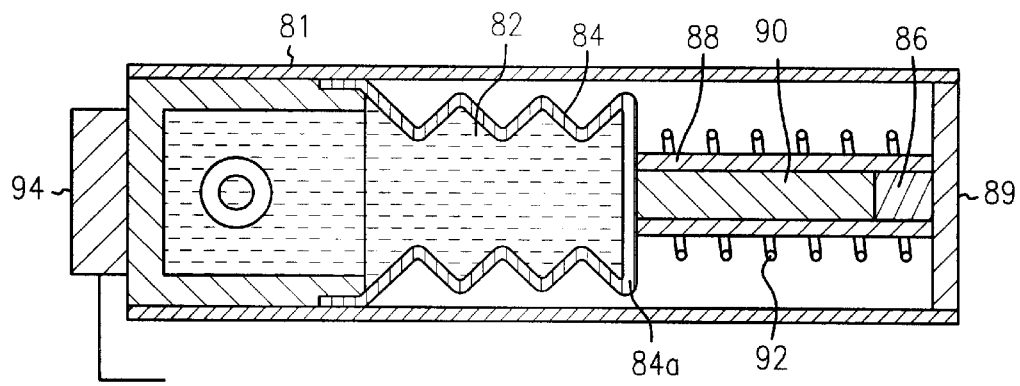
FIG. 13 is a cross-sectional view taken along lines 13—13 of FIG. 12.
Figure 14:
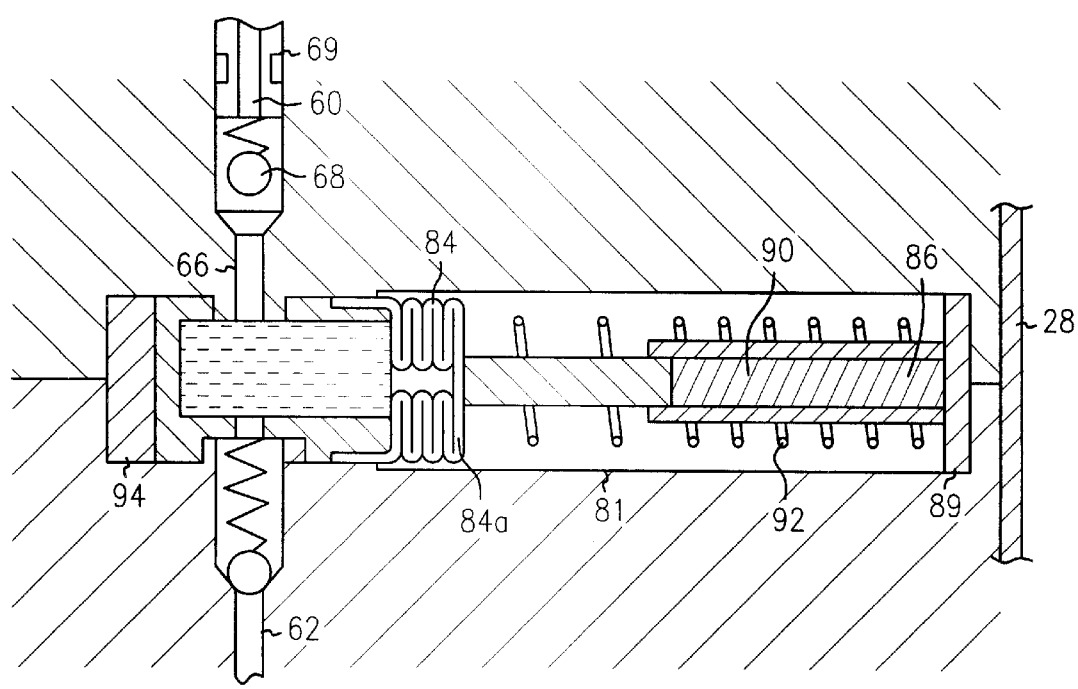
FIG. 14 is a cross-sectional view similar to FIG. 13 but showing the magnetically expandable gel in an expanded configuration following delivery of a bolus dose of medication to the patient.

Bellows 84 is movable by the second stored energy source of the invention from the first expanded configuration shown in FIG. 12 to the second collapsed configuration shown in FIG. 14. This important second stored energy means here comprises a magnetically stimulated gel 86 that is contained within a generally cylindrically shaped housing 88 that is closed at one end by an end plate 89. Also housed with housing 88 is a pusher member 90 which is disposed in engagement with the base 84a of bellows 84. Biasing means, shown here as a coil spring 92, surrounds housing 88 and functions to continuously urge bellows 84 toward the collapsed configuration shown in FIG. 14.

Also forming a part of the bolus delivery means of this form of the invention is a second stimulation means for stimulating the magnetically stimulated, polymer gel 86. This second stimulation means here comprises magnetic means, provided in this instance as an electromagnet 94 which is connected to one end of housing 81 in the manner best seen in FIGS. 12, 13 and 14. Electromagnet 94, when energized, stimulates gel 86 in a manner to cause it to expand in the manner shown in FIG. 14. As the gel expands, it will act on pusher member 90 urging it to the left as viewed in FIG. 14 and causing it to collapse bellows 84. As bellows 84 collapsed the fluid contained within reservoir 82 will be caused to flow under pressure into passageway 66 and then outwardly of the device via check valve 68 and outlet 60. However, check valve 68 is designed to prevent fluid flow in the opposite direction toward reservoir 82.

Considering now, in greater detail, the novel expandable mass or polymeric gel 86, like gel 70, gel 86 is of a semisolid form that can advantageously be handled without external containment under ambient manufacturing conditions. As before, phase transition gels are best suited for use in constructing the magnetically expandable mass of the present invention. As previously mentioned, these types of gels undergo a change in polymer conformation and in so doing exhibit a large volume change at a given phase-transition condition. Unlike liquids, which exhibit a fixed temperature for state of vaporization to a known volume and with such vaporization point changing as a function of ambient pressure, the phase-transition gels in this invention are multicomponent polymers which can be made to respond with various volume changes to a singular external stimuli, in this case a magnetic stimulus.

Examples of a number of different types of phase-transition gels suitable for the present application are disclosed in the previously identified patents which are hereby incorporated by reference herein. As was the case with gel 70, the magnetically responsive gel 86 may be reversibly responsive.

Gels particularly well suited for use as the stored energy sources of the present invention include various types of so called ferrogels that respond reversibly to a magnetic field. In this regard, it is has long been recognized that such gels can be used in order to conduct mechanical work as illustrated by M. Zrinyi et. al (*Macromolecules* 1998, 31, 6541; *Colloid Polym Sci* 2000, 278,98; *Polym. Gels Networks* 1997, 5, 415; *J. Intel. Mater.* 1998, 9, 667). These gels are typically composed of a polymeric network that is swollen by a "ferrofluid". The ferrofluid is a dispersion of nano-sized (colloidal) magnetic particles suspended in a liquid medium. Typical ferrofluids are composed of magnetite particles ($Fe_3O_4$) but, as noted by Zrinyi (*J. Intel Mater.* 1998, 9, 667), any suitable colloidal magnetic particle could be employed. Indeed, ferrogels made from hybrid organic-inorganic hydrogels and maghemite ($\gamma$-$Fe_2O_3$) nanoparticles have also been reported (Cabuil, V. *Angew, Chem. Int. Ed. Engl.* 1999, 38 3672). Preparation of the ferrofluid is typically done by precipitating the magnetic particles in a solvent medium. The precipitation step to make the colloidal dispersion of magnetic particles can be before, during or after cross-linking reactions used to form the polymeric gel network (Zrinyi, *Polym. Gels Networks* 1997, 5, 415). For example, the ferromagnetic colloids can be precipitated within the confines of a preformed polymeric gel. Alternatively, cross-linking of the polymers and monomers can be done in the presence of the collodial particles.

Polymers typically used for such magnetically responsive gels are chemically cross-linked polyvinyl alcohol and poly (N-isopropylacrylamide), which are both well know in the literature to form hydrogels. By way of non-limiting example, typical polymer systems know to form gels are: disubstituted acrylamides cross-linked with such agents as ethylene glycol diacrylate (EGDA), di(ethylene glycol)bis (allyl carbonate) (DEGBAC), methylenebis(acrylamide) (bis), ethylene glycol dimethacrylate (EGDMA), and mixtures there of. Other common gel systems are: polyethylene glycols, polysaccharides and cellulose ethers, and hybrid organi-inorganic hydrogels such as those described in Cabuil, V. *Angew. Chem. Int. Ed. Engl.* 1999, 38, 3672.

A ferrogel can respond to a magnetic stimuli by either elongating (growing in length) or contracting (shortening in length). As described in Zrinyi, *Polym. Gels Networks* 1997, 5, 415, the placement of the applied magentic field relative to the ferrogel determines whether a contraction or elongation is observed. If the ferrogel is cylindrical in shape and fastened at one end, and the magnetic field is placed below the tip of the unfastened end of the gel, an expansion will occur. Conversely, if the magnetic field is placed in the middle of this fastened gel, a contraction will occur. It is noteworthy that typical magnetic field strengths used to induce these types of expansions and contractions are very small, and on the order of normal permanent magnets (approximately 300 millijoules (mT)). It has also been determined (*Polym. Gels Networks* 1997, 5, 415) that the elongation of a ferrogel is dependent on the concentration of magnetic particles in the ferrofluid. For example, doubling the concentration of magnetic species in a ferrogel will cause a greater than fourfold increase in the elongation length. In effect, to achieve greater elongation in a ferrogel, one increases the amount of ferromagnetic particles in the gel. Additionally, the degree of elongation in a ferrogel can be controlled by altering the amount of cross-linking in the polymer and the amount of current flowing through the electromagnet that induces the applied magnetic field (*Polym. Gels Networks* 1997, 5, 415).

Ferrogels are also unique stimuli-responsive polymer gels because of their fast response times. In particular, ferrogels are known to respond nearly instantaneously and reversibly to magnetic stimuli. This property, and those described above, allow the use of ferrogels to produce mechanical work. For example, using a 300 mT applied magnetic field, a 1.5 g cylinder of ferrogel was shown to lift an 11 g. weight. Under the conditions employed, this displacement corresponds to approximately 5 millijoules (mT) of mechanical work (Zrinyi, SPIE on Electroactive Polymer Actuators, P. 406). Thus, using ferrogels as stored energy means to conduct mechanical work is quite plausible.

Considering next the novel fill means of the invention for filling first and second reservoirs 44 and 82, this important means here comprises a fill line 96 that is interconnected with a fill port 98 formed in cover block 67 by means of a threaded fitting 97. Fill port 98 communicates with reservoir 44 via a fluid passageway 99 and a check valve 100 which is held in position within block 67 by fitting 97. Connected at the distal end of fill line 96 is a fill septum assembly 104 that includes a base 104a and pierceable septum 104b (FIG. 1) that can be accessed by a hypodermic needle of a conventional syringe. As shown in FIG. 3, fill septum assembly 104 can be implanted at a convenient location remote from the implanted housing 28. With this arrangement, a hypodermic needle can be inserted through the skin to introduce into reservoirs 44 and 82, via septum 104b and fill line 96, a quantity of liquid medicament such as heparin, morphine, insulin or like medicament. As can be seen by referring to FIG. 4, once reservoir 44 is filled, reservoir 82 will also fill via passageway 62 and check valve 64 which will move into an open position as a result of fluid pressure exerted on the check valve by overflow of fluid from reservoir 44. However, check valve 64 is constructed and arranged to prevent fluid flow in the opposite direction.

Figure 5:
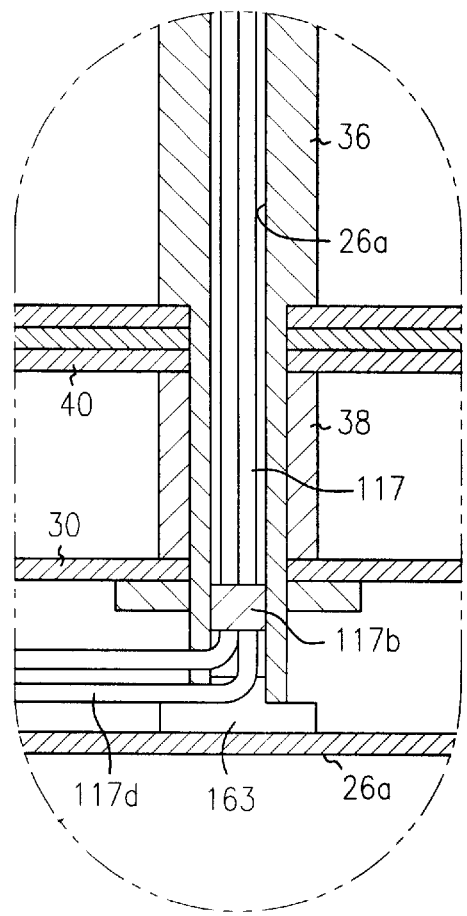
FIG. 5 is an enlarged, cross-sectional view of the area designated as "5" in FIG. 4.
Figure 15:
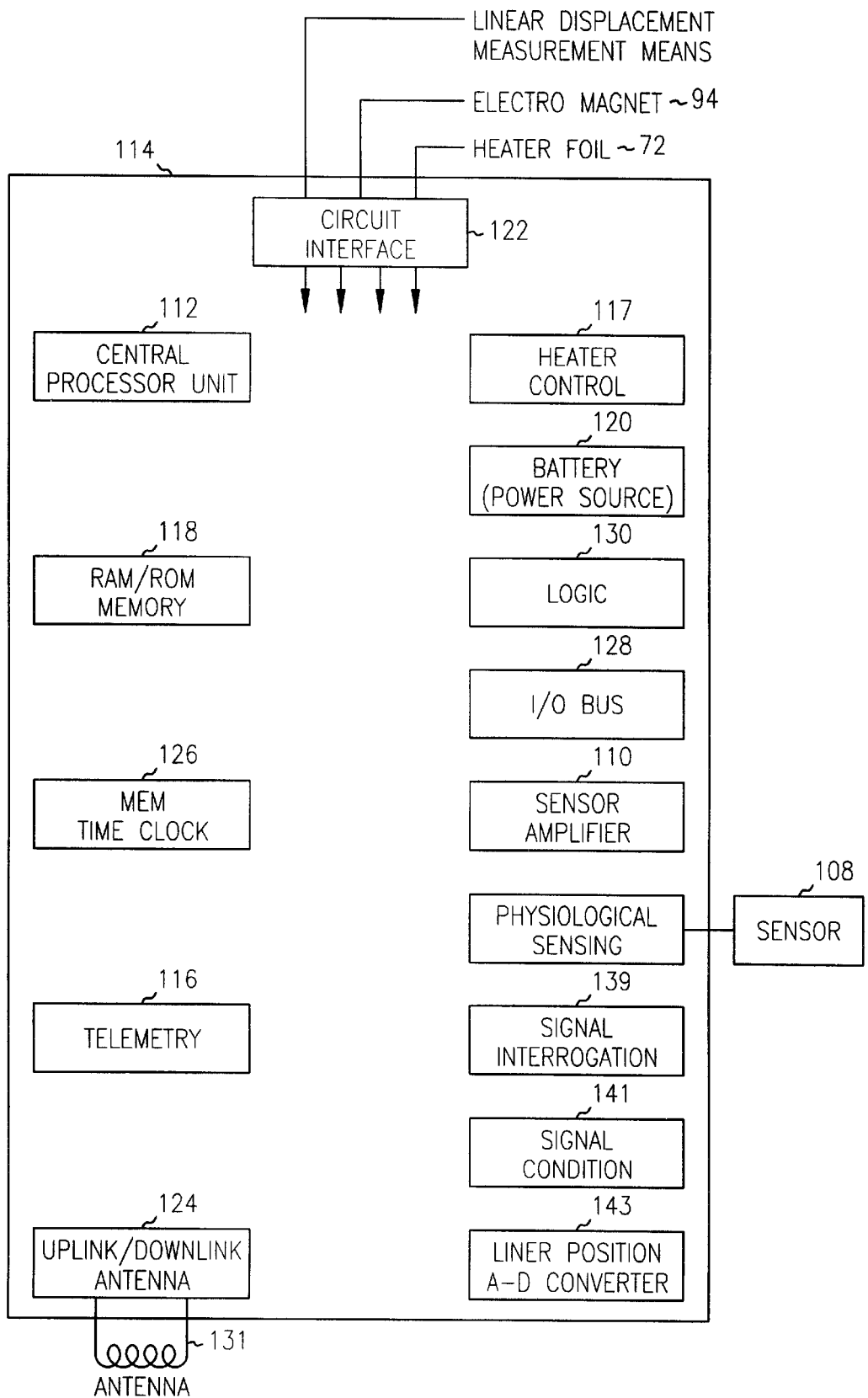
FIG. 15 is a generally diagrammatic view showing the relationship among the various components of the controller and stimulation means of the invention.

Also forming an important aspect of the present invention is the provision of sensor means for sensing various body conditions of the patient. This sensor means here comprises a sensor line 106 that is connected to housing 28 by means of a threaded fitting 107 in the manner illustrated in FIG. 4. Connected to the distal end of sensor line 106 is an In vivo, physiological sensing tip generally designated as 108 that is capable of detecting and responding to the physiological, physiochemical, chemical, optical and electronic changes in the patient's body or bloodstream. The physiological sensing tip 108 and its sensing structure may comprise an electronic, chemical or optical interface designed to measure specific parameters or changes in parameters and to compare known values combined within the associated delivery system electronic memory. Sensing tip is interconnected with the PC board 30 by sensor wiring 109 that extends downwardly through a central passageway 36a formed in shaft 36 (see FIG. 5). It will be clear to those skilled in the art that, when the physiological sensing portion is coupled directly or indirectly with a sensing amplifier 110 such as shown in FIG. 15 and with the controller means of the invention which includes a central processing unit (CPU) 112, various physiological or chemical changes may be sampled and compared with known parameters set forth in a look-up table carried in device memory. This important controller means, or controller system 114 of the invention, the details of which will later be described, is shown in schematic form in FIG. 15 of the drawings.

In operating the apparatus of the invention, the CPU 112 of the controlling system 114 can be programmed to execute a command function signal to initiate control and/or terminate the timed operation and frequency of the first and second stimulation means and can also be responsive to the physiological/chemical sensor circuitry of the sensor means in a manner to provide an interactive operating mode of operation of the delivery system. For example, a heater control 72b can be used to energize heating foil 72.

Other sensors operably coupled with the CPU/electronic controller 112 and, with the earlier-mentioned linear displacement measuring means of the invention, are provided and used to determine such things as reservoir volume, delivery rate over time, battery life, system temperature and the like. Alarm data can also be provided as, for example, reservoir condition and component malfunction.

Figure 7:
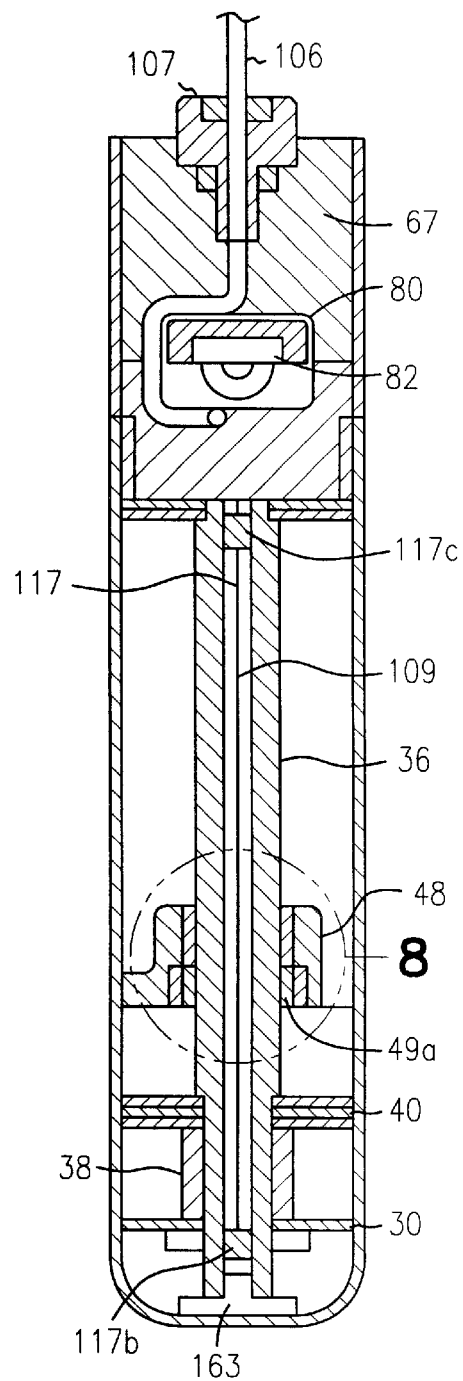
FIG. 7 is a cross-sectional view taken along lines 7—7 of FIG. 4.
Figure 8:
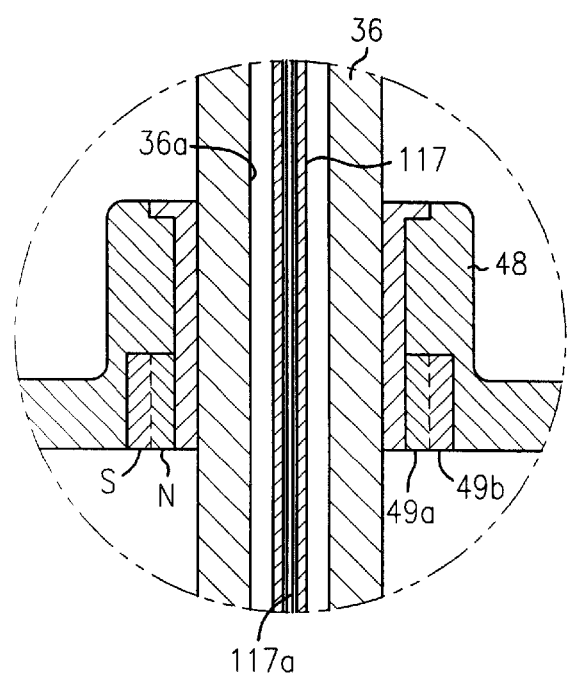
FIG. 8 is an enlarged, cross-sectional view of the area designated as "8" in FIG. 7.
Figure 8A:
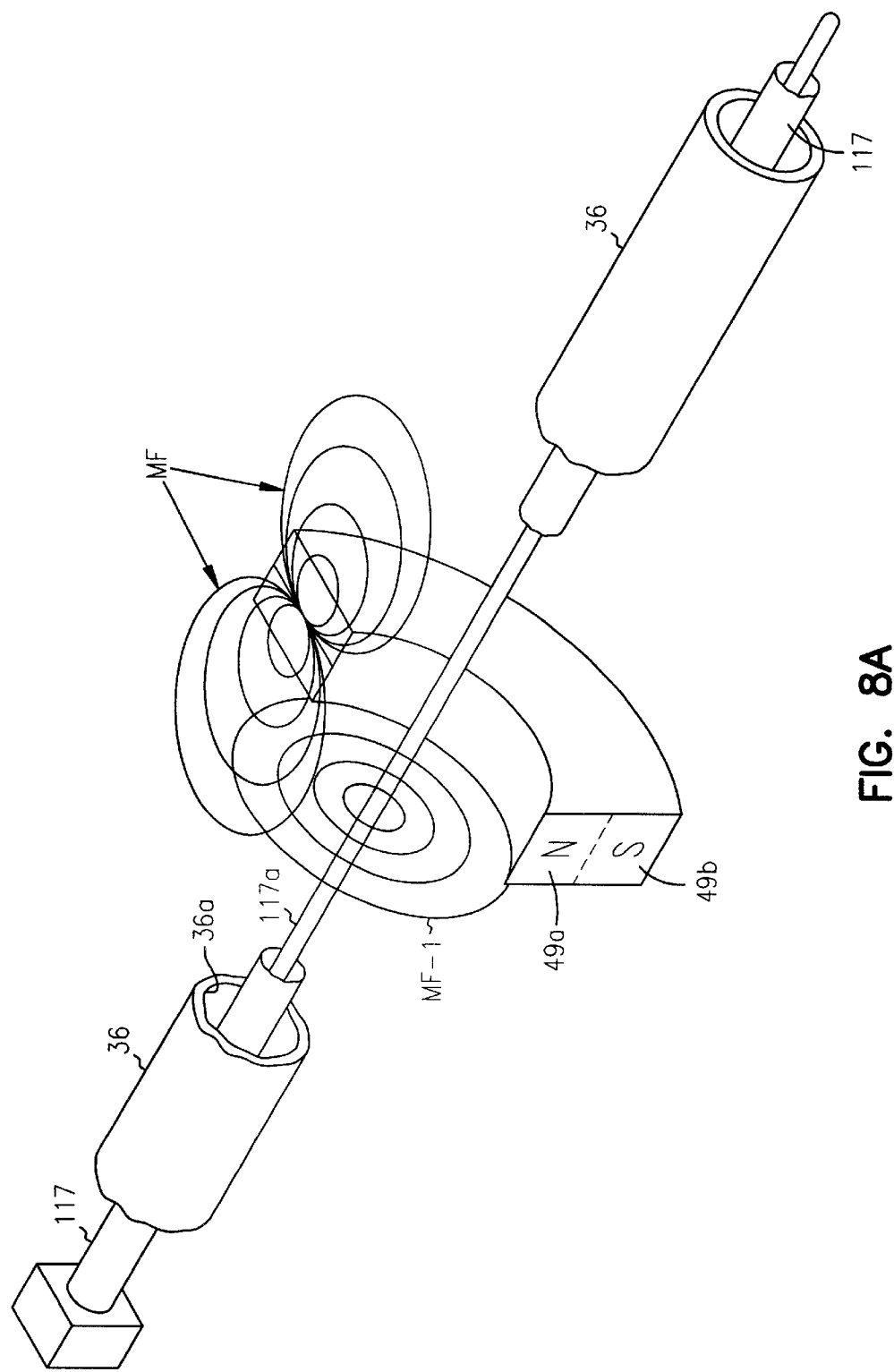
FIG. 8A is a generally perspective, illustrative view showing the operation of the linear displacement means of the invention for determining the volume of medicament remaining in the basal delivery reservoir.

Considering specifically the important linear displacement measuring means of the invention for precisely determining at any point in time, the volume of fluid remaining in reservoir 44. The construction of this unique means is best seen by referring to FIGS. 7, 8, and 8A. As shown in FIGS. 8 and 8A, magnet 49 has a north and south pole 49a and 49b that creates a magnetic field "MF" that emanates from the magnet as depicted in FIG. 8A. In operation of the linear displacement measuring means of the present form of the invention, an interrogation pulse is launched along a conductive wire 117a carried within a magnetostrictive waveguide 117 that is housed within the central passageway 36a of shaft 36 and supported by a lower head 117b and an upper anchor element 117c (FIG. 4). Waveguide, or magnetostrictive element 117 here comprises a nickel-ferrous alloy tube that is disposed within passageway 36a. Launching of the interrogation pulse creates an instantaneous magnetic field "MF-1" along the active length of a shaft 36 (FIG. 8A). This magnetic field "MF-1" then interacts with the magnetic field "MF" emanating from the magnet that is attached to capture housing 48. The effect of the two magnetic fields is to generate a magnetostrictive strain wave below the magnet which travels at sonic speed through the waveguide medium and is detected by the cooperatively associated electronics of the apparatus mounted on circuit board 30 via head 117b and connector 117d that is connected to circuit board 30. The position of the magnet on the capture housing 48 is determined by measuring the elapsed time between the launching of the interrogation pulse and the detection of the strain pulse. In essence, a sonic delay line is created which allows the position of magnet 49 to be determined to a resolution of up to 2.5 μm depending upon output signal type and stroke length. The result is a very precise, reliable, real time and repeatable determination of the volume of medicinal fluid remaining in reservoir 44.

Linear position transducers of the general type described in the preceding paragraphs are commercially available from sources such as Balluff of Florence, Ky. and MTS Systems Corporation of Cary, N.C. Publications of the companies should be consulted for a more detailed description of the linear displacement measuring means of the invention.

The telemetry assembly 116 of the electronic circuitry of the apparatus (see FIG. 15) relies on the use of a radio frequency transmission system that is commercially available and well known to those skilled in the art. With the use of such a system, it is possible to up link the system performance, event history data residing in the receiving register and other operating parameters and current values such as the remaining drug volume and battery life. Additionally, the telemetry assembly can receive down link programming instructions upon proper interrogation and address confirmation in the programmable system operating mode. Such programming changes of function and operating values can be implemented and recorded within the delivery system electronics controller memory. This program can also be accomplished through the use of an operably associated portable system programmer and programming head which can be readily adapted from commercially available systems that are well known to those skilled in the art.

Figure 16:
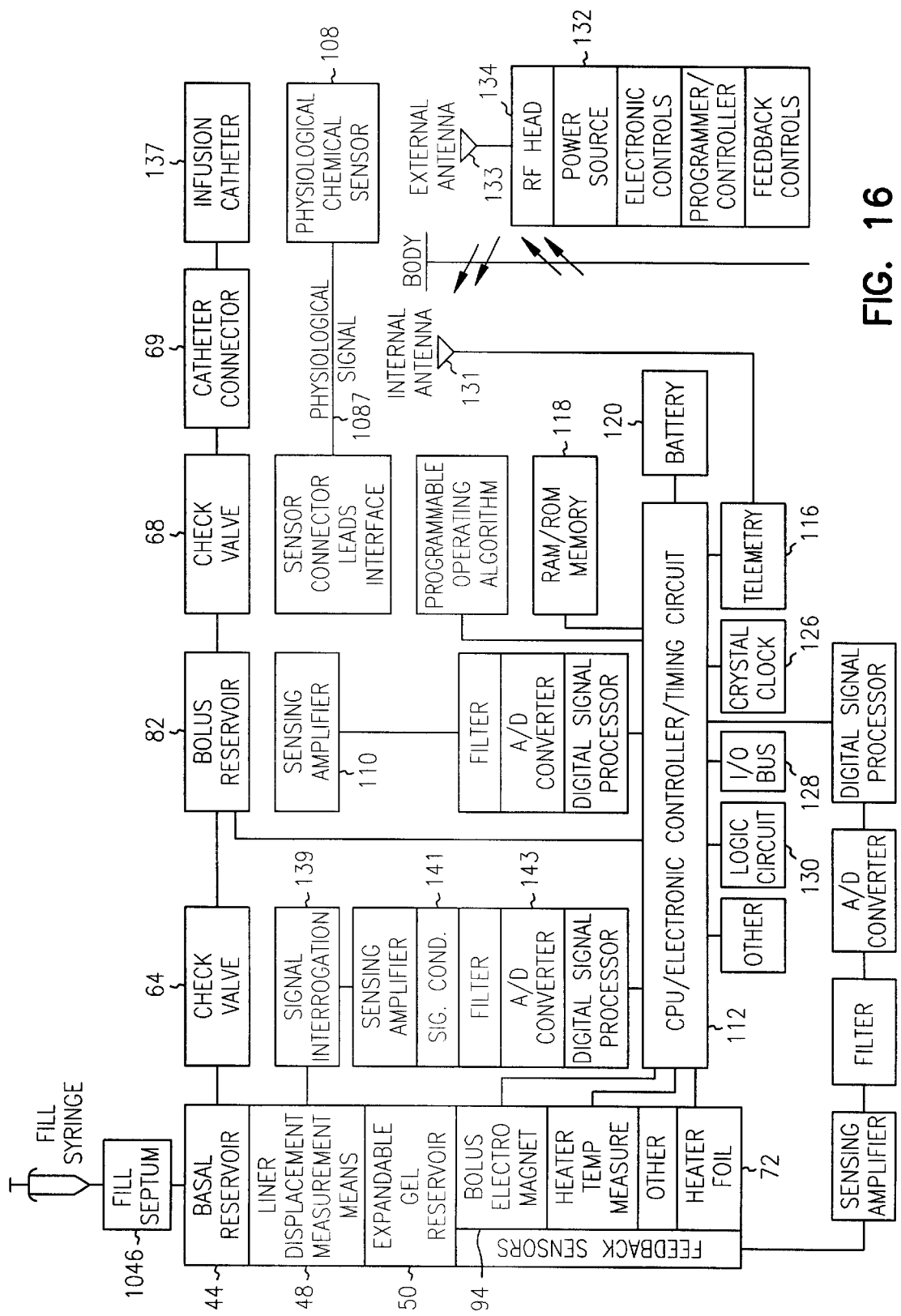
FIG. 16 is a generally diagrammatic view, further illustrating the relationship among the various operating components of the apparatus of the invention.

In preparing the apparatus of the invention for use, the controller means is initially programmed in accordance with instructions from the treating physician. As illustrated in FIG. 15, the controller means here comprises, in addition to the previously identified central processing unit 112 and telemetry assembly 116, a RAM/ROM memory 118, a power supply, or battery 120, feed back electronics, various amplifiers, such as amplifier 110, a circuit interface 122, an antenna coupler 124, a real time clock 126, an I/O bus 128, logic circuits 130, timing and control switch matrix circuits and various related circuitry. Further details concerning the controller means and its relationship with the operating components of the delivery device, including the earlier described sensor means, are also shown in block diagram form in FIG. 16. More particularly, this figure shows the relative relationship among the previously described fill means of the device, the fluid reservoirs, the device gel reservoirs, the heat source, the catheter, the linear displacement measurement means, position signal interrogation 139, position signal condition 141, and liner position A-D converter 143. Additionally, FIG. 16 illustrates, in block diagram form, the relationship among these components and the various components and related systems that make up the electronics of the device that are mounted on the PC board 30, including the central processing unit, the RAM/ROM memory, the digital signal processor, the logic circuit, and the telemetry assembly. As previously mentioned, the various electronic components of the device are well known to those skilled in the art and their interconnection and programming to meet the various requirements of the physician and patient protocol are well within the capability of the skilled artesan.

Figure 1:
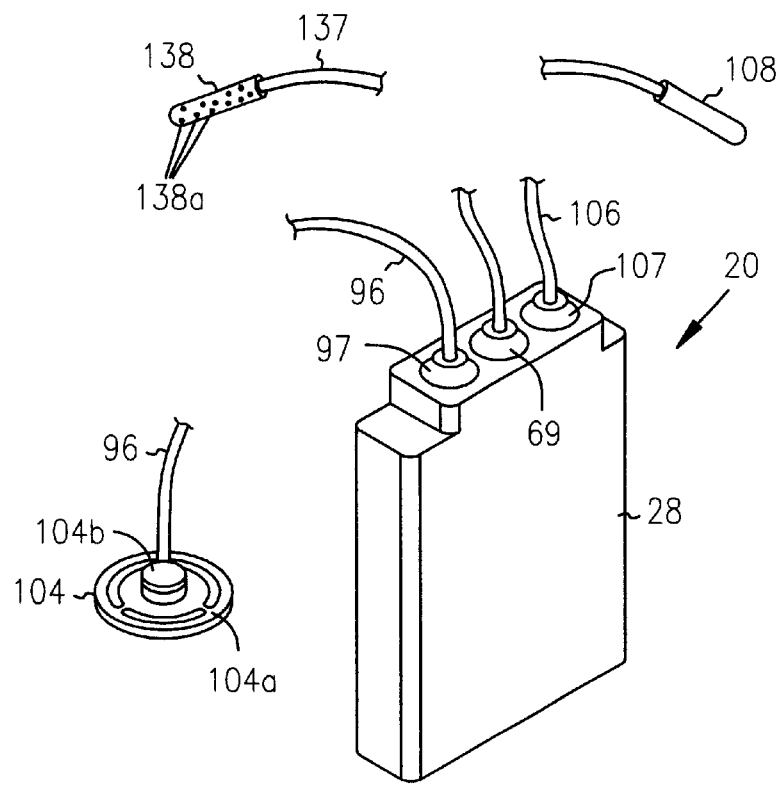
FIG. 1 is a generally perspective view of one form of implantable medicament delivery device of the invention.
Figure 2:
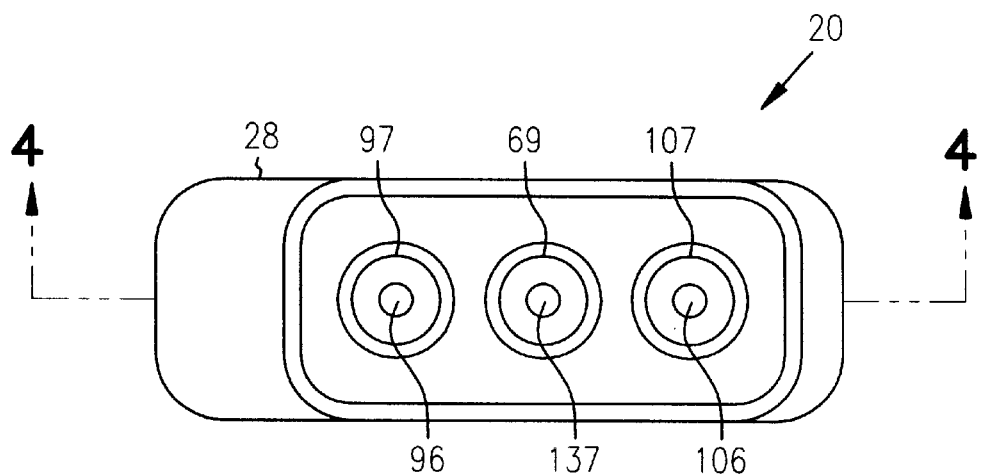
FIG. 2 is a top plan view of the delivery device shown in FIG. 1.

Upon filling the basal and bolus reservoirs 44 and 82 using the fill means of the invention and after the controller means is initially programmed, the device can be implanted into the patient in the manner shown in FIG. 3. This done, the antenna means and the frequency transmitting means of the invention are used to commence the basal medicament delivery to the patient by energizing the heater foil 72. The antenna means here comprises a power receiving antenna 131 (FIG. 15) for receiving power from the radio frequency transmitting means which here comprises an external power source 132 and a transmitting antenna 133 that is operably connected to an RF head 134 and related programmer and feed back controls of conventional construction (FIG. 16). Antenna 133 transmits power to antenna 131 through conduction coupling or coupler 124 (see FIGS. 15 and 16). Antennas 131 and 133 are of a conventional construction well known to those skilled in the art. In one form of the invention, power source 132 is operable to produce radio frequencies in the desired telemetry range so that when antenna 133 is positioned proximate antenna 131 and is inductively coupled therewith, signals can be delivered to the CPU/electric controller 112 of the implanted device to accomplish, among other things, the energization of heater foil 72. Upon energizing the heater foil 72, the expandable gel 70 will expand into the configuration shown in FIG. 10 causing fluid to be controllably expelled from the device via the infusion means of the invention which here comprises an infusion line, or cannula 137 that is connected to housing 28 by means of fitting 69 in the manner shown in FIG. 4. Provided at the distal end of cannula line 137 is a porous infusion tip 138 that permits fluid flow outwardly through small outlet passageways 138a formed in the tip (FIG. 1). Cannula 137 is strategically positioned at the time of implant of the device to deliver the medicament to a selected therapeutic site within the patient's body by means of porous tip 138.

When it is desired to deliver a bolus dose of medicament to the patient, the antenna means and the frequency transmitting means are used to energize electro-magnet 94 via leads 94a (FIG. 9) which are connected to CPU/Electronic Controllers 112 (FIG. 16). Upon energizing electromagnet 94, the bolus expandable gel 86 will expand into the configuration shown in FIG. 14 causing a bolus dose of fluid to be controllably expelled from the device via cannula 137 of the infusion means of the invention.

Figure 17:
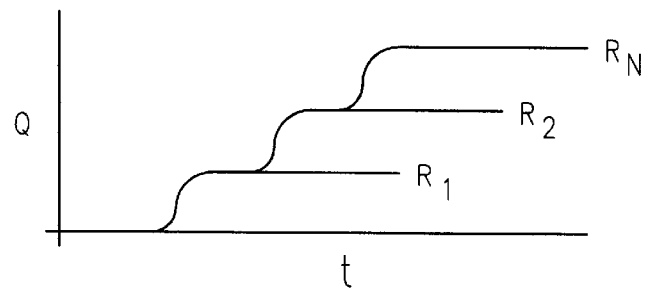
FIG. 17 is a generally diagrammatic view showing the ability of the device of the invention to deliver controlled basal doses of medicament to the patient at selected intervals.
Figure 17A:
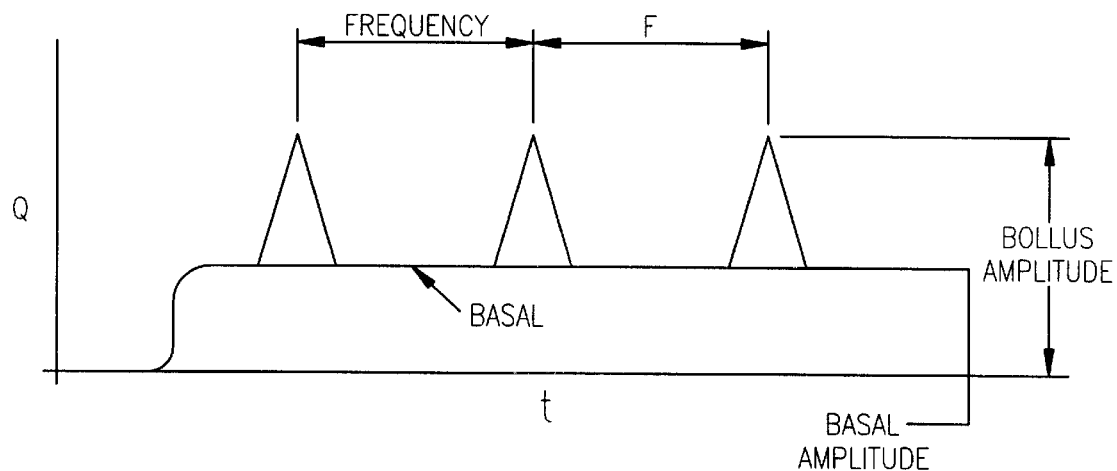
FIG. 17A is a generally diagrammatic view illustrating the ability of the device of the invention to deliver both basal doses of a controlled volume and bolus doses of a controlled volume and at selected intervals of time.

With regard to both the basal and bolus delivery of medicament to the patient, it can be observed by referring to FIGS. 17 and 17A that the controller means can be programmed to deliver basal doses to the patient at predetermined volumes and at various intervals R1, R2, and RN as may be desired by the physician. Similarly, by appropriate programming of the controller means, bolus doses of medicament can be delivered to the patient in controlled volumes or quantities at selected frequencies in the manner illustrated in FIG. 17A via preprogrammed protocol or under independent external interrogation. Should a different bolus dose from that shown in FIG. 17A be desired, the bolus flow can be controlled by appropriately changing the bolus reservoir configuration.

Figure 20:
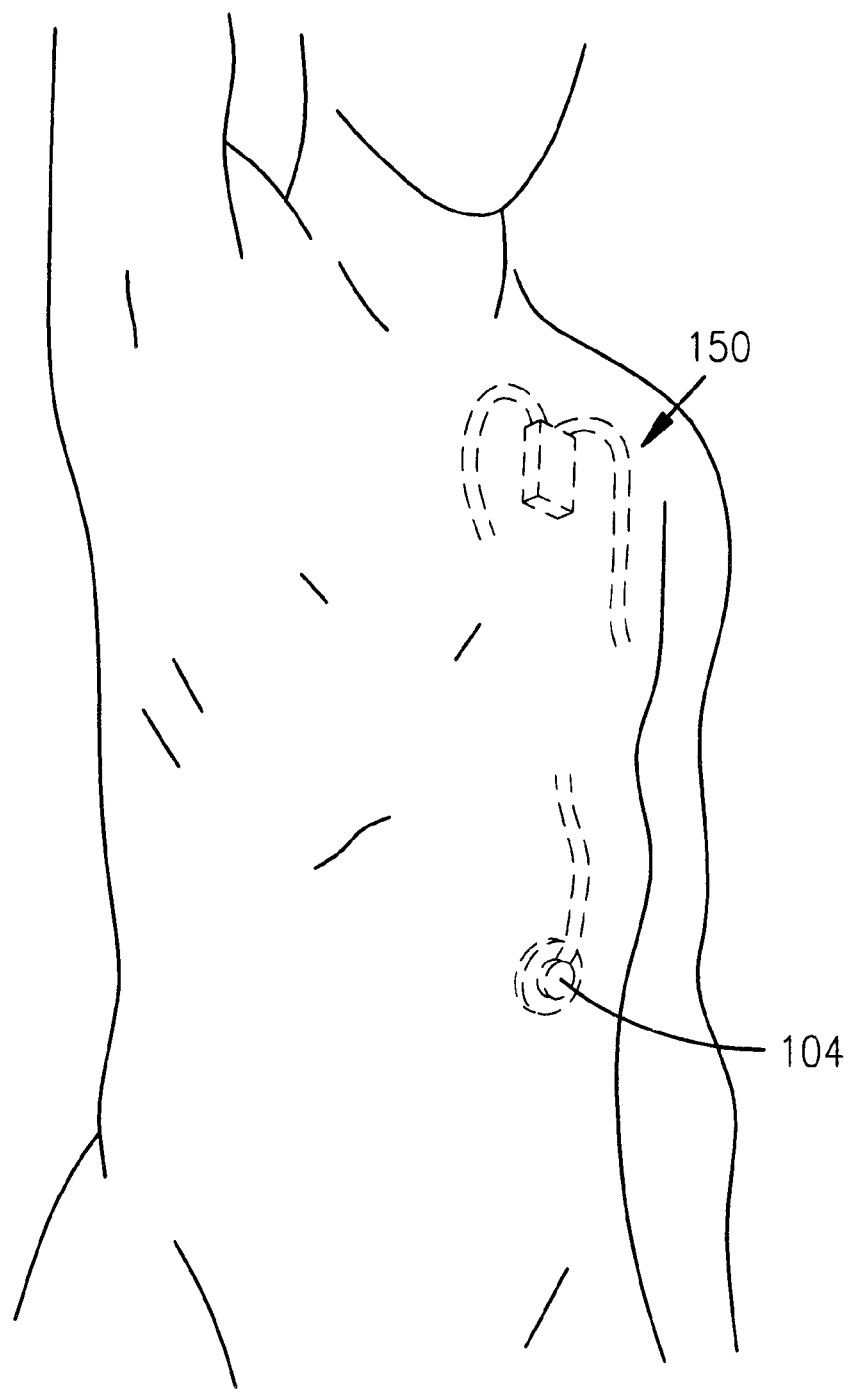
FIG. 20 is a generally perspective, illustrative view showing the delivery device of FIG. 18 implanted within the patient's body.

Referring next to FIGS. 18 through 31, an alternate form of the apparatus of the invention is there shown and generally designated by the numeral 150. As illustrated in FIG. 20, this embodiment of the invention is also adapted to be implanted into the body of the patient. The apparatus of this latest form of the invention is similar in general configuration and internal construction to that shown in FIGS. 1 through 17 and like numerals are used in FIGS. 18 through 31 to identify like components. As before, the apparatus comprises a base assembly 152 and a cover assembly 154 that are encapsulated within a thin metal casing 26, which includes a lower portion 26a and an upper portion 26b which are interconnected to form the hermetically sealed housing 28 of the device. The primary difference between this second embodiment of the invention and the embodiment earlier described is that stored energy source of the basal delivery subsystem comprises a light activated gel and the stored energy system of the bolus delivery subsystem comprises a unique electro-responsive gel laminate.

Like base assembly 22 of the earlier described embodiment, base assembly 152 comprises a first printed circuit (PC) board 156 which is mounted on a lower tie plate 158 and is interconnected with a second PC board 160 by means of a pair of transversely spaced-apart threaded support shafts 162 and 164. Connected to the lower extremity of each of the shafts 162 and 164 is an elastomeric insulator foot 163. PC board 156 is spaced from the tie plate 158 by spacers 166 and PC board 160 is spaced from PC board 156 by spacers 168. Mounted on PC boards 156 and 160 are various electronic components of the apparatus, the character of which will later be described. Where required, the electronics of the apparatus, including those mounted on the PC boards can be housed within a protective beryllium copper shield which provides interference immunity. Tie plate 158 is also connected to a fitting block 170 by threaded shafts 162 and 164. Positioned between PC board 160 and fitting block 170 is a first fluid reservoir 172 as well as the first stored energy means of the invention for controllably expelling fluid from first reservoir 172 at a precise delivery rate.

Figure 21:
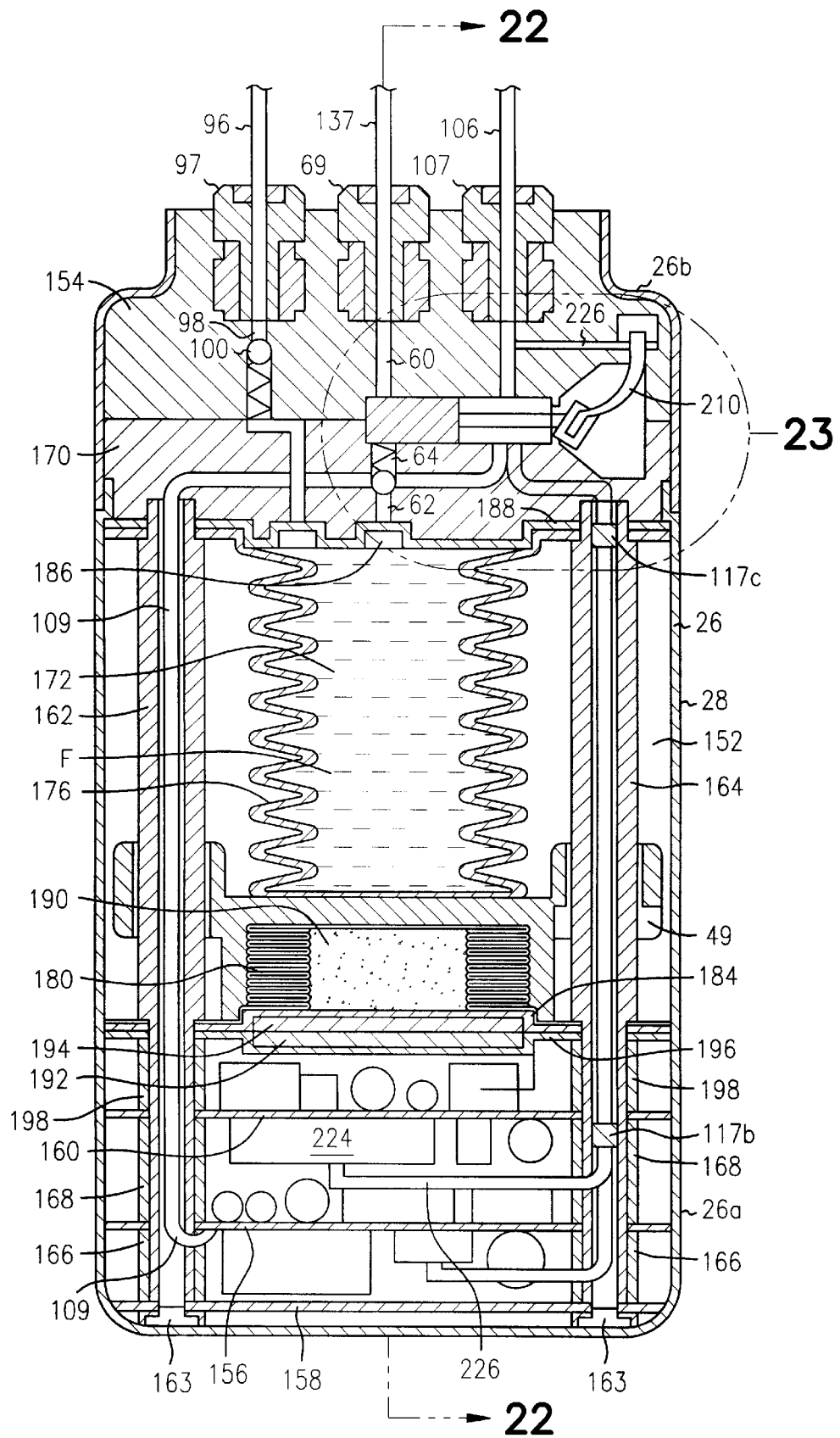
FIG. 21 is a cross-sectional view taken along lines 21—21 of FIG. 19.
Figure 22:
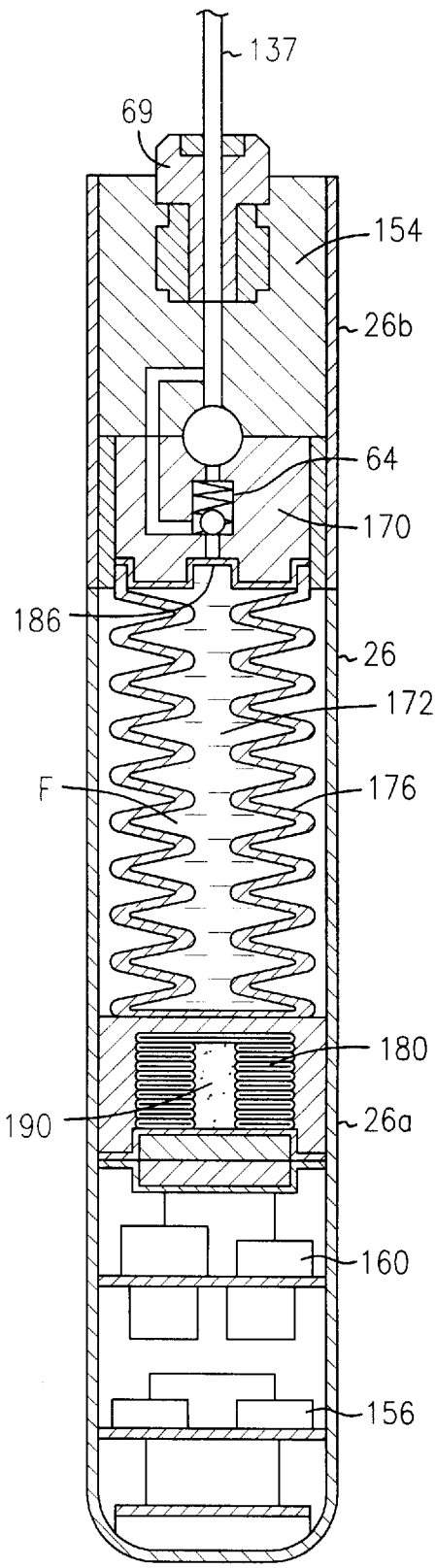
FIG. 22 is a cross-sectional view taken along lines 22—22 of FIG. 21.

First fluid reservoir 172, which contains the medicinal fluid "F" to be delivered to the patient, is defined by an expandable component, here provided as a first expandable bellows 176. In a manner presently to be described, bellows 176 is movable between the expanded configuration shown in FIG. 21 and the collapsed configuration shown in FIG. 24. Disposed between bellows 176 and the first stored energy means of the invention is a capture housing 178 which is slidably connected to shafts 162 and 164 for movement between a first lowered position shown in FIG. 21 to a second upraised position shown in FIG. 24. Capture housing 178, which is of similar construction to capture housing 48, receives a second expandable component or bellows housing 180 that contains the first stored energy means of the invention (FIG. 21). As in the earlier embodiment of the invention, described, bellows housing 180 is expandable from a first collapsed configuration shown in FIGS. 21 and 22 to the expanded configuration shown in FIG. 24. As bellows housing 180 moves into its expanded configuration, capture housing 178 slides upwardly along shafts 162 and 164 into the upraised position shown in FIG. 24. Connected to capture housing 178 is a ring magnet 49 that slides along shaft 164 as the capture housing moves upwardly and downwardly. As before, ring magnet comprises a part of the linear displacement measuring means of the invention for measuring the volume of medicament within fluid reservoir 172. The linear displacement measuring means of this latest embodiment is of identical construction and operation to that previously described herein.

Figure 23:
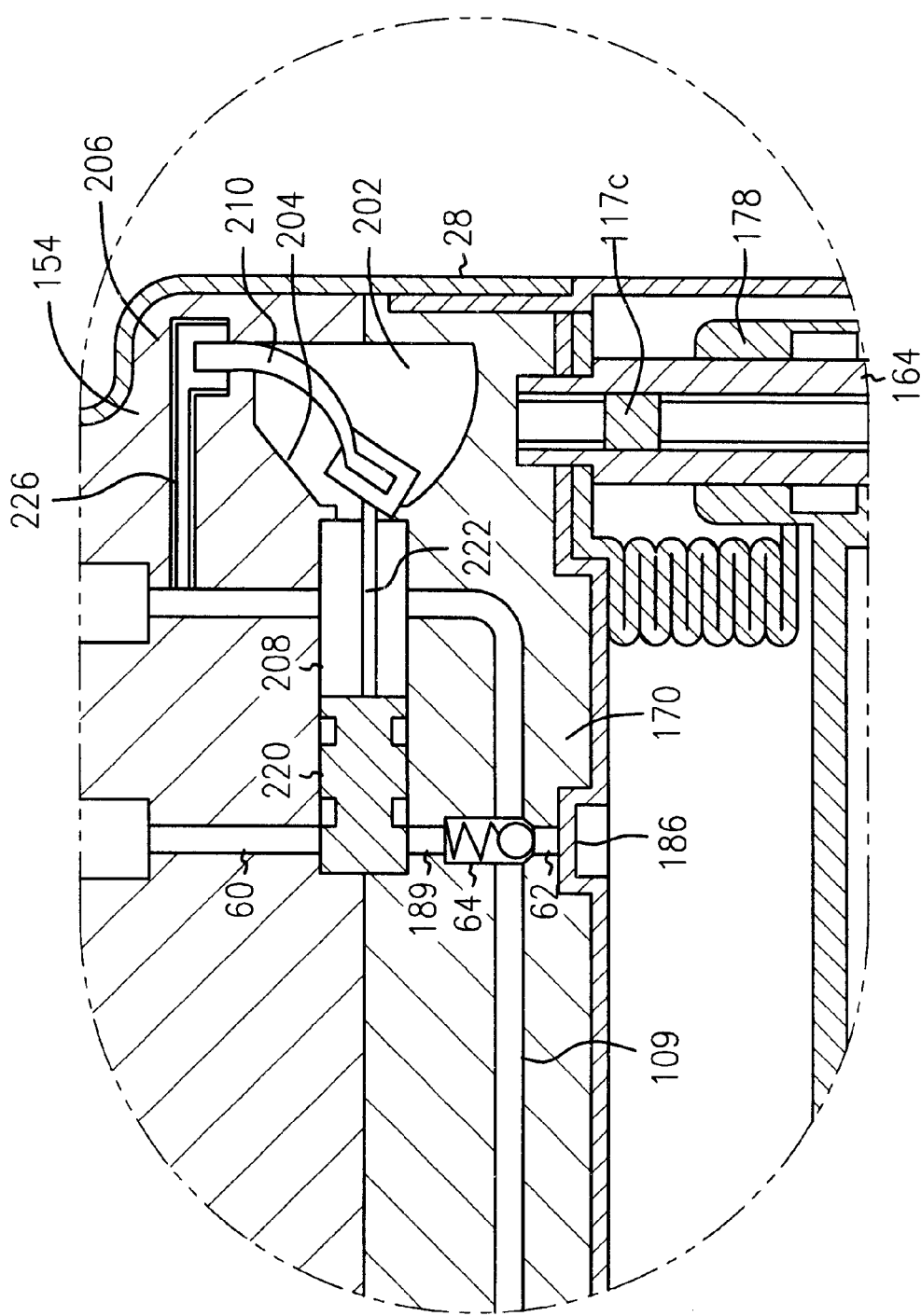
FIG. 23 is an enlarged, cross-sectional view of the area designated as "23" in FIG. 21.

Located between PC board 160 and a bellows cover plate 184 that closes the lower end of bellows 180 is the important first stimulation means of this latest form of the invention for stimulating the first stored energy means. As before, the stimulation means functions to stimulate the first stored energy means in a manner to cause it to expand. Expansion of the first stored energy means causes bellows 180 to expand in the manner shown in FIG. 24 and concomitantly causes capture housing 178 to slide upwardly along shafts 162 and 164. This upward movement of capture housing 178 causes bellows 176 to collapse into the configuration shown in FIG. 24. As bellows 176 collapses, the fluid contained therein is forced outwardly of the fluid reservoir through an outlet port 186 formed in a bellows cover 188 which closes bellows 176 (FIG. 21). Outlet port 186 communicates with outlet 60 of housing 28 via a first passageway 62, formed in fitting 170, via check valve 64 mounted within fitting 170, via a second passageway 189 formed in fitting 170 and via a second bolus reservoir, the character of which will presently be described (FIG. 23).

Figure 27:
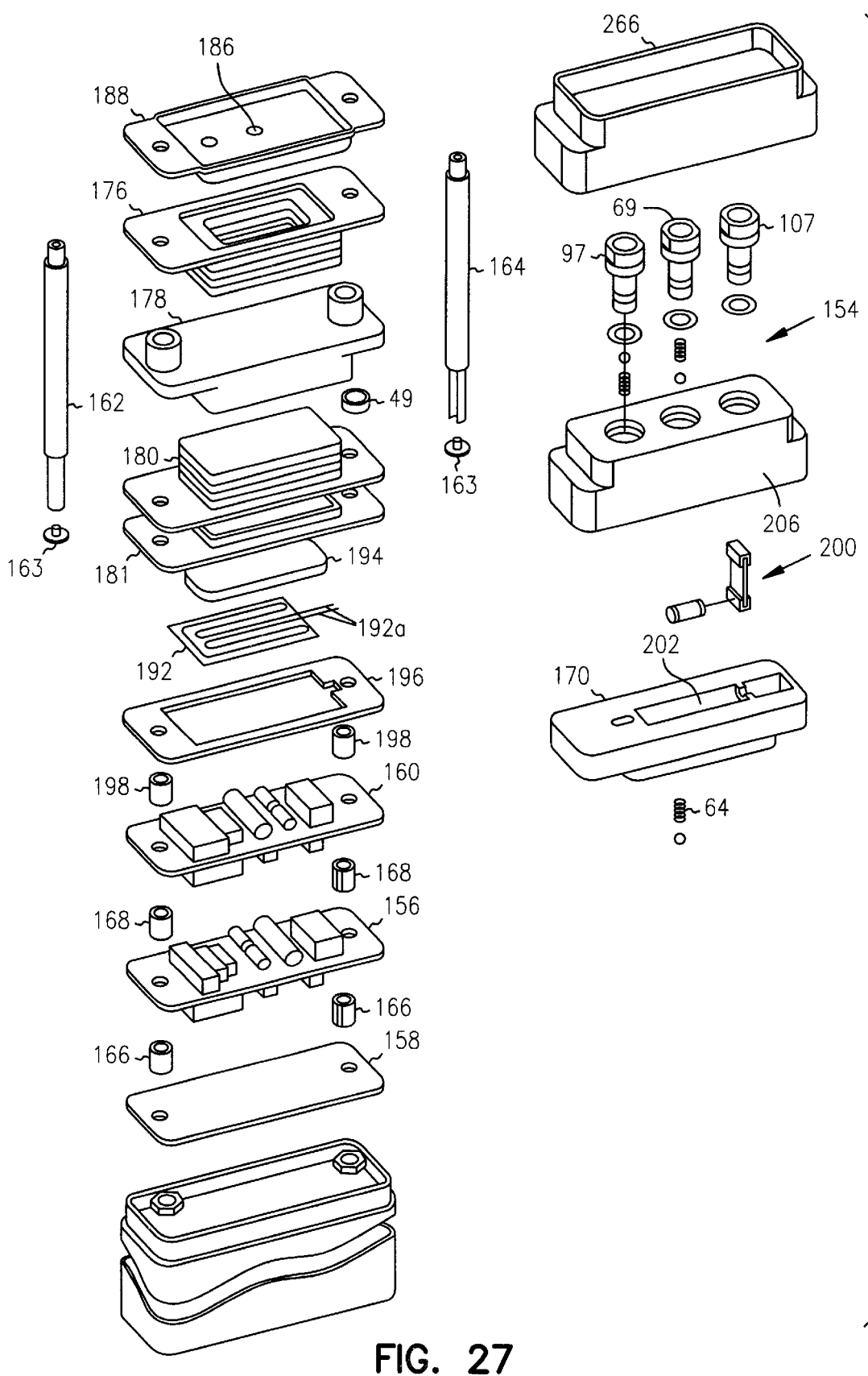
FIG. 27 is a generally perspective, exploded view of the assembly shown in FIG. 21.

Considering now the first stimulation means of the invention for stimulating first stored energy source, which here comprises a light responsive, expandable mass or gel 190. This novel stimulation means here comprises a source of light namely a light sheet 192, that is disposed between expandable gel 190 and second PC board 160. Light sheet 192 is commercially available from sources including Light sheet Systems of Nashua, N.H. and comprises a flexible electroluminescent film having, a micro-thin layer of light-generating phosphor compound laminated within electrically-conductive and insulating materials. In a manner presently to be described, power is supplied to the light sheet through two terminals 192a which are mounted at one end thereof (FIG. 27). When the light sheet is energized, light is distributed across the entire sheet, charging the internal phosphor layer to a light-emitting state causing the light sheet to emit a bright white light over substantially its entire surface. The manner of energizing the light sheet will be described hereinafter. The color and intensity of the light source can be appropriately tailored to the required local level of environmental requirement. Additionally, to control the wave length of light reaching gel 190, an optical wave length filter 194 is provided between a lower light sheet cover 196 that is spaced apart from second PC board 160 by spacers 198 and bellows plate 184 that is connected to bellows 180 (FIGS. 21 and 27). It is to be understood that any suitable source of light having the required wave length and intensity can be used in lieu of light sheet 192.

Expandable mass or gel 190 can be formed from a number of polymer gels of the character discussed in the Tanaka patents and previously considered herein connection with the discussion of the various candidate energy sources suitable for use in the first embodiment of the invention. However, polymer gels of particular interest for use as the first stored energy source of this latest form of the invention include "four-armed" polyethylene glycol (PEG) gels discussed in an article entitled "Light-Induced Tailoring of PEG-Hydrogel Properties" by Fotios M. Andreopoulos, et al in *Biomaterials* 19 (1998) 1343–1352. As discussed in this article, when the hydroxyl termini of PEG gels are functionalized with cinnamylidane acetate groups, photosensitive PEG macromers (PEG-CA) are formed. Upon radiation of the macromers, crosslinks are formed between adjacent cinnamylindene groups resulting in highly crosslinked networks which exhibit photoscissive behavior upon exposure of UV irradiation (254 nm). These PEG gels as well as the others discussed herein are cited by way of example and not by way of limitation.

While the PEG gels in themselves do not exhibit reversible swelling upon exposure to UV light, they can be modified to do so by copolymerization with UV sensitive monomers.

Other polymer gel systems that could swell reversibly, would incorporate UV active monomers of the character previously described as phase transition gels. For example, Tanaka et al has copolymerized the Leuco derivative into acrylamide gels in the manner earlier discussed herein.

Another suitable photoactive monomer based on the azobenzene derivative $CH_2CHC(O)C_6H_4N=NC_6H_5$ has also been incorporated into UV active phase transition gels as demonstrated by M. Irie in *New Functional Materials*, Volume B in an article entitled "Photo-and Chemical-Responsive Polymer Solution and Gel Systems".

Suitable monomers for copolymerization with the UV active monomers previously mentioned are: first common methacrylates such as hydroxymethacrylate (HEMA) n-isopropylacrylamide (NIPPAAm), N, N'-methylenebis (acrylamide) (BIS) and other commercially available acrylate and methacylate monomers. Polyethylene glycolmethacrylate (PEGMA) could also be copolymerized with the UV active monomers mentioned in the preceding paragraphs.

Polyethylene oxides (PEGs) can also be used in modified form to act as crosslinkers in polymerizations to form photoactive gels. For example, commercially available PEGs of the character previously described herein can be modified to yield PEG-diamines for copolymerizaton with acrylates following the protocol described by Mooney, (Macromolecules, 1999, Volume 32, P. 5561). Other methacrylate derivatized polymer gels that should allow facile incorporation of the photoactive monomers include glycidyl methacrylate-derivitized dextran (see Hennink, W. E., Macromolecules, 1997, 30, 4639.); lactose-based homopolymers in the presence of an acrylate crosslinker (see Zhau, W. J, Macromolecules, 1997, 30, 7063) and polyethylene glycol diacrylates (PEGDA) (see Cha Hesj, P. R. Macromolecules, 1996, 29, 1976). The photoactive monomers could also be polymerized with a vinyl lactam such as N-vinylcaprolactam in the presence of a standard crosslinker such as a vinyl pyrolidone.

Figure 26:
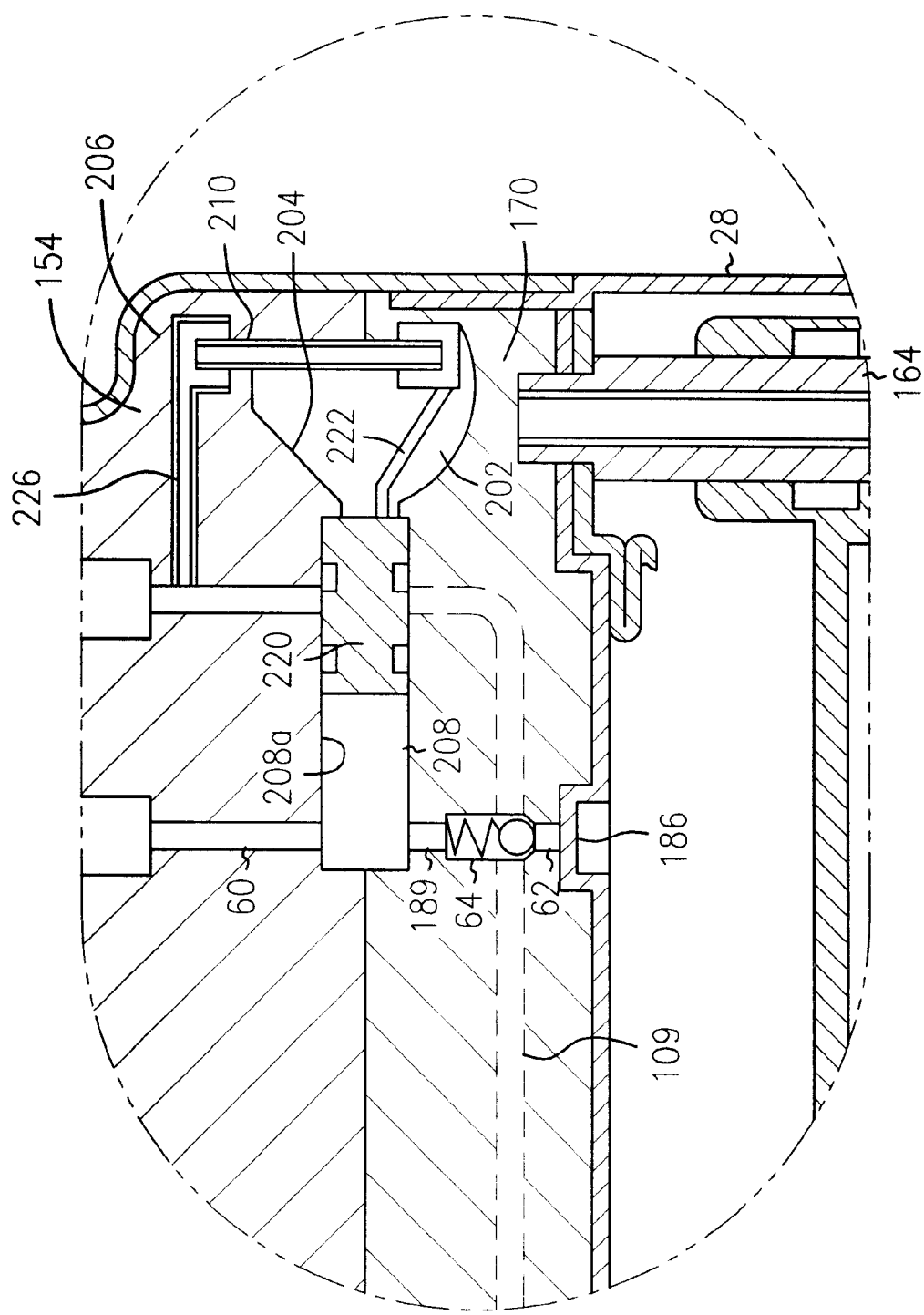
FIG. 26 is a cross-sectional view similar to FIG. 23, but showing the bolus delivery subsystem in a starting configuration.

Considering next the novel bolus delivery subsystem of the latest form of the invention, this novel subsystem comprises a delivery assembly 200 that is disposed within a cavity 202 formed in fitting block 170 and within a cooperating cavity 204 formed in a cover block 206 (FIGS. 21 and 26). Cavities 202 and 204 cooperate to define an elongated reservoir cavity 208, the inboard portion of which defines the previously mentioned bolus or second reservoir 208a (FIG. 26). As best seen in FIG. 23, reservoir 208 is disposed intermediate of and in communication with fluid passageway 189 and outlet 60. Reservoir 208a contains the same medicinal fluid as is contained within reservoir 172, but, in a manner presently to be described, can be delivered to the patient as bolus doses of a controlled volume. This delivery of bolus doses of medicament to the patient is accomplished through stimulation of the second stored energy means of the invention, the character of which will next be described.

Figure 28:
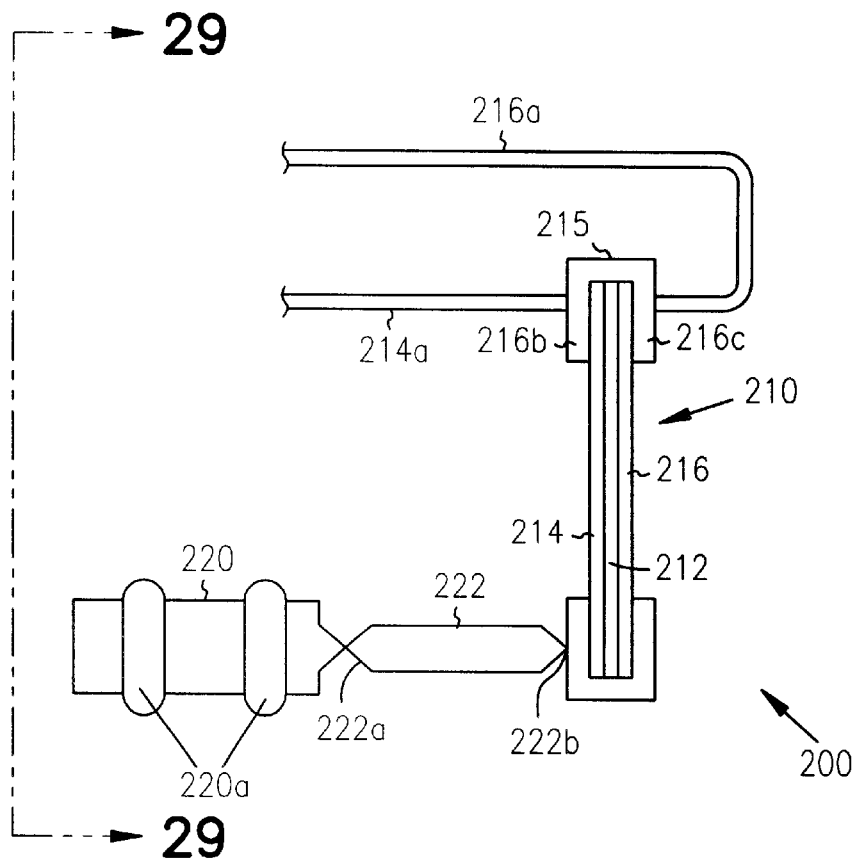
FIG. 28 is an enlarged, fragmentary, side-elevational view of a portion of the of the bolus delivery subsystem of the apparatus.
Figure 29:
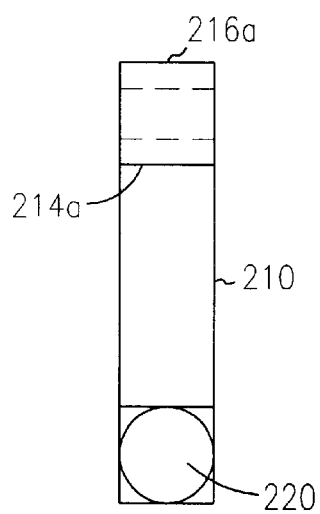
FIG. 29 is a view taken along lines 29—29 of FIG. 28.

The highly novel second stored energy means of this latest form of the invention comprises an electro-responsive, flexible bolus laminate actuator 210 which is of the construction best seen in FIG. 28. As there shown, laminate 210 uniquely comprises a solid polymeric electrolyte 212 disposed between first and second electrically conductive polymers 214 and 216 respectively. In the instant form of the invention, the conductive polymers 214 and 216 are formed from polypyrrole (PPy) while electrolyte 212 is formed from poly(epichlorohydrin-co-ethylene oxide) [P(ECH-co-BO)]/ $LiClo_4$. One method of making the conducting polymers 214 and 216 as well as the method of making the electrolyte 212 used to construct laminate 210 is discussed in an article entitled *A Solid State Artificial Muscle Based on Polypyrrole and a Solid Polymeric Electrolyte Working In Air* and authored by Sansinena, Olazabal, Otero, Fonseca and DePaoli (see Chemical Communications, 1997 pp. 2217 and 2218) and reference should be made to his article for further details as to the nature of these materials.

As shown in FIGS. 23, 26, and 28, laminate 210 is affixed at one end to a bolus piston 220 by means of a connector 222 (FIG. 28).

In operation of the bolus delivery system of the invention, oxidation of the polymeric actuator will cause $ClO_4$ ions to enter the PPy film, thereby making its volume increase. During reduction, the $ClO_4$-ions leave the PPy film and the volume of this film shrinks. This increase and decrease in film size results in a bending motion of the triple layer laminate. Mobility of charge throughout the triple layer is facilitated by the ability of the ions in the solid polymeric electrolytes to move about freely.

As best seen in FIG. 28, connector 222 includes living hinge mechanism portions 222a and 222b that are so constructed and arranged as to permit the movement described in the preceding paragraph and to allow laminate 210 to move from the first, substantially planar configuration shown in FIGS. 26 and 28 to the second, curved configuration shown in FIG. 23. It is to be understood the various types of hinge and linkage mechanisms well known in the art could be used in place of living hinge portions 222a. As indicated in FIG. 23 bolus piston 220, which is reciprocally movable within the inboard portion of cavity 208, will move from the first outboard location illustrated in FIG. 26 to the second inboard location shown in FIG. 23 when laminate 210 moves toward its second, curved configuration. As bolus piston 220 moves toward its second location, the fluid contained within reservoir 208a will be urged outwardly of the reservoir into outlet 60 and then into the infusion means of the apparatus which is of identical construction and operation to that previously described herein. Bolus piston 220 is provided with co-molded protuberances 222a which function as a slidable seal as the piston reciprocates within reservoir 208a.

Movement of the laminate 210 from the first configuration shown in FIG. 26 to the second fluid expelling configuration shown in FIG. 23 is caused by the bolus stimulation means of the invention next to be described. Turning particularly to FIG. 28, it is to be noted that conducting polymer 214 is positively charged while conducting polymer 216 is negatively charged thereby causing a constant flow of current through the laminate. Due to the character of the novel polymeric materials that make up laminate 210, this constant current flow will cause the laminate to yieldably deform or bend in the manner shown in FIG. 23. However, due to the resilient nature of the laminate materials, upon an interruption in current flow, the laminate will return to the generally planar starting configuration as shown in FIG. 26 and, in so doing, will also return bolus piston 220 to its starting location. Reference should be made to the previously cited Sansinena article for more details concerning the nature and operation of laminate 210.

Considering next the bolus stimulation means of the invention for causing current flow through laminate 210. This novel means here comprises a source of electric current such as a battery 224 that is carried by PC board 160. Battery 224 is interconnected via the CPU/Electronic Controller carried by PC board 160 with leads 214a and 216a of delivery assembly 220 by means of a connector wire 226. Leads 214a and 216a are electrically coupled with laminate 210 via an upper laminate connector block 215 that comprises electrical interface connectors 216b and 216c. As shown in FIGS. 21 and 23, wire 226 extends downwardly of hollow support shaft 164 for interconnection with PC board 160. Battery 224 may also be used to supply electrical power to light sheet 192 via leads 192a (see also FIG. 25). As previously discussed stimulation of laminate 210 by causing a current to flow therethrough will cause the laminate to yieldably deform, or bend, in the manner shown in FIG. 23, which, in turn, will force the bolus piston 220 to the left as viewed in FIG. 23 forcing the bolus fluid within reservoir 208a into outlet 60.

Figure 18:
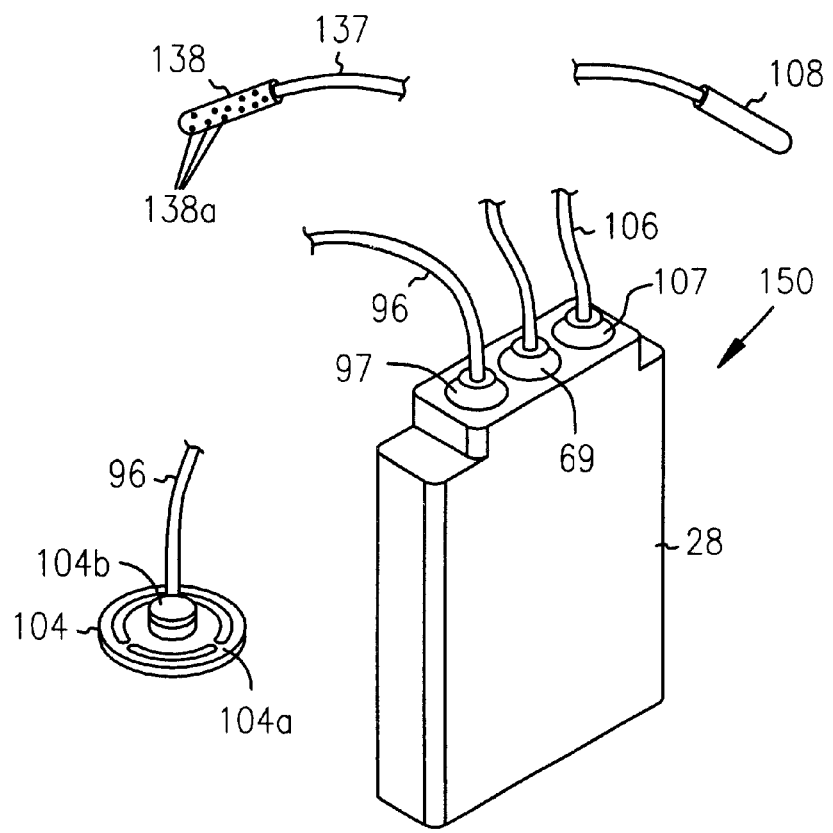
FIG. 18 is a generally perspective view of an alternate form of implantable medicament delivery device of the invention.
Figure 19:
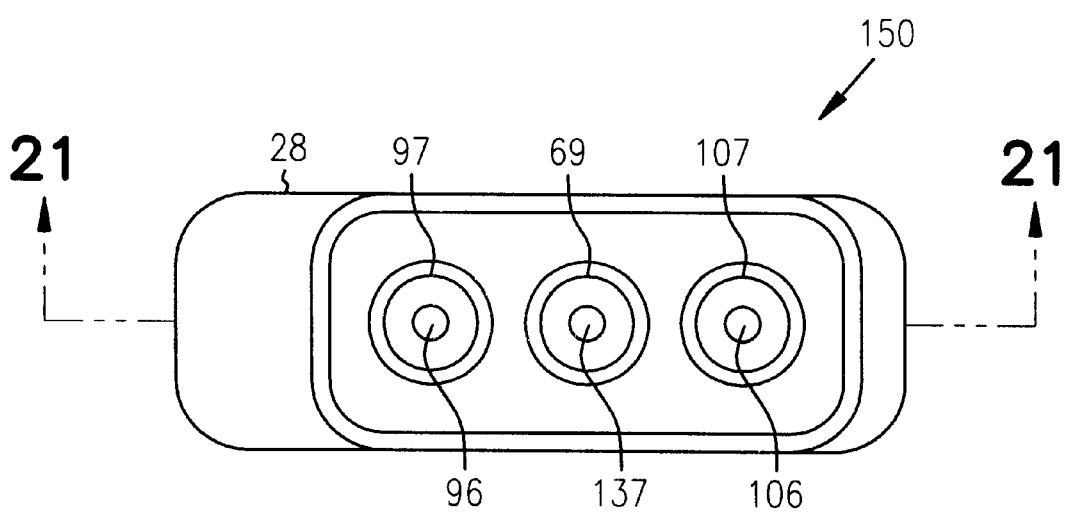
FIG. 19 is a top plan view of the delivery device shown in FIG. 18.

As illustrated in FIGS. 18 and 21, the fill means of this embodiment of the invention is connected to cover 154 and functions to controllably fill reservoirs 172 and 208a. This fill means, which comprises fill line 96 and fill septum assembly 104 is identical in construction and operation to the fill means described in connection with the embodiment of the invention shown in FIGS. 1 through 17.

Also connected to cover 154 is the sensor means of the invention for sensing various body conditions. This sensor means, which comprises sensor 108 and connector line 106, is also identical in construction and operation to that previously described.

Figure 30:
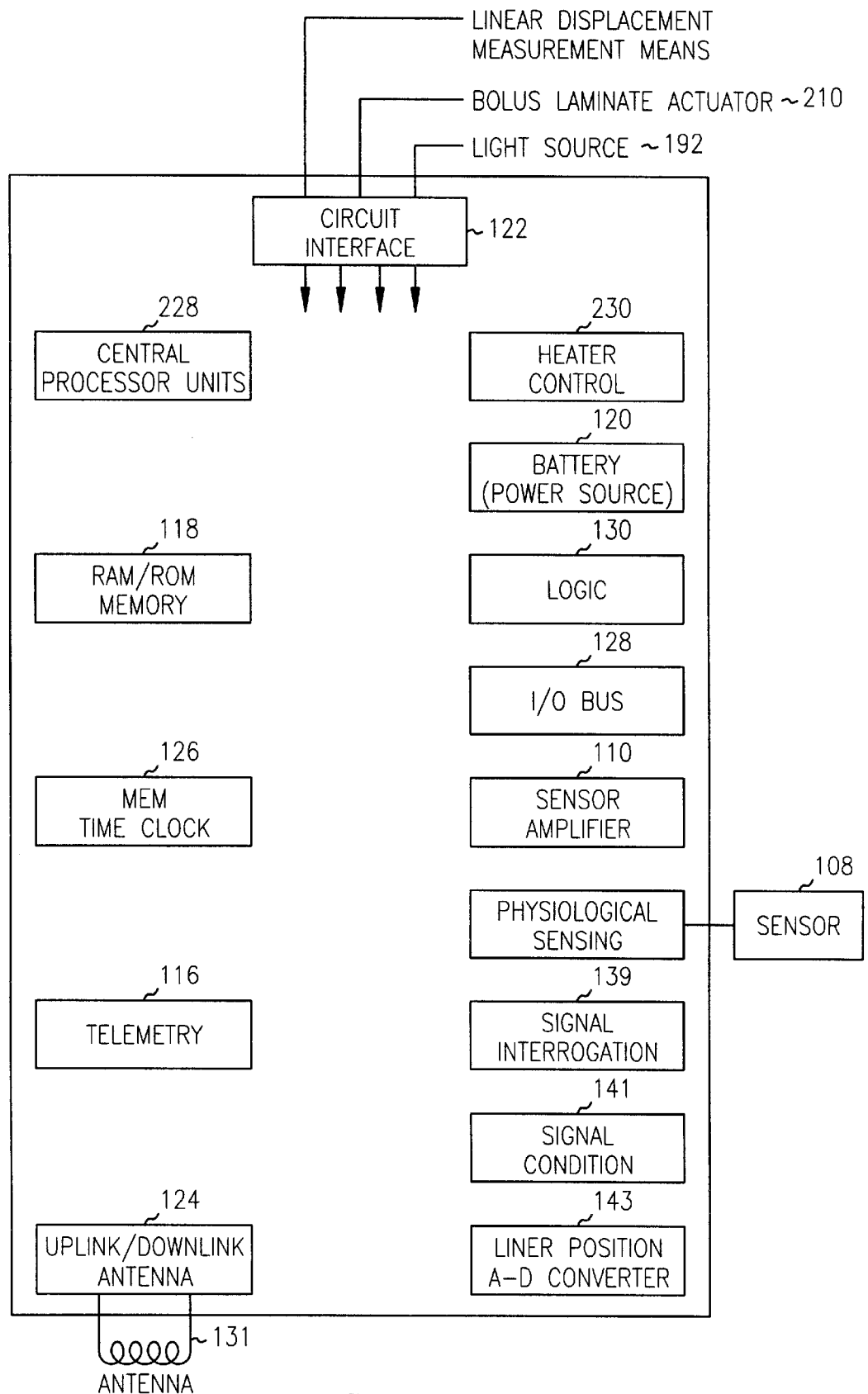
FIG. 30 is a generally diagrammatic view showing the relationship among the various components of the controller and stimulation means of this latest form of the invention.
Figure 31:
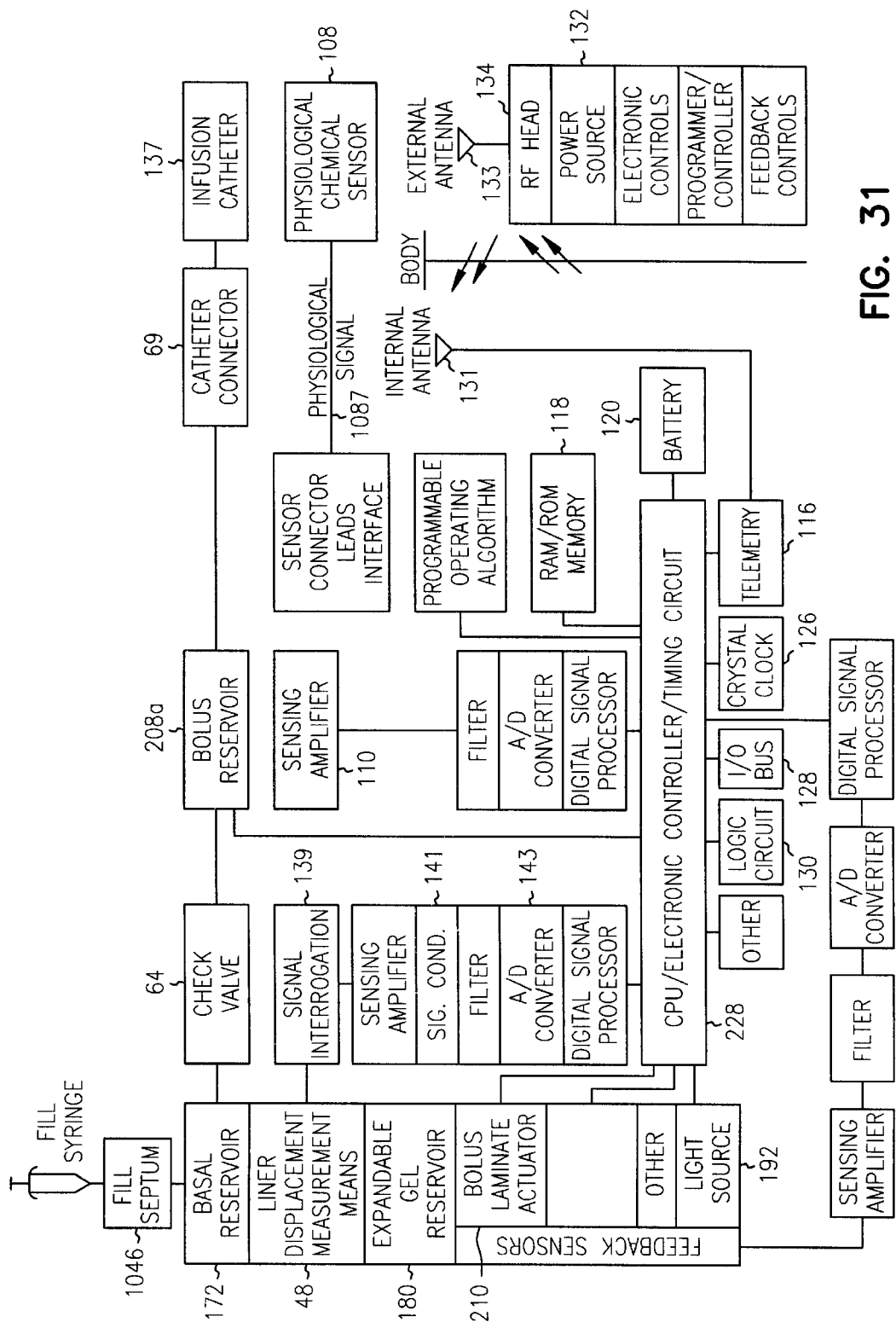
FIG. 31 is a generally diagrammatic view, further illustrating the relationship among the various operating components of the apparatus of this latest form of the invention.

In operating the apparatus of this latest form of the invention, the CPUs carried by the circuit board 156 and 160, which comprise a part of controlling system 228 (FIGS. 30 and 31) can be programmed to execute a command function signal to initiate control and/or terminate the timed operation and frequency of the first and second stimulation means of the apparatus and can also be responsive to the physiological/chemical sensor circuitry of the sensor means in a manner to provide an interactive operating mode of operation of the delivery system. For example, a light control 230 can be used to energize light sheet 192 via leads 192a (FIGS. 30 and 31).

As in the earlier described embodiment of the invention, other sensors operably coupled with the controlling system and with the linear displacement measuring means can be provided and used to determine such things as drug volume, delivery rate over time, battery life, system temperature and the like. Alarm data can also be provided as, for example, reservoir condition and component malfunction.

The telemetry assembly 116 of the electronic circuitry of the apparatus which is basically identical to that described in connection with the embodiment of FIGS. 1 through 17, relies on the use of a radio frequency transmission system of the character previously described that is commercially available and well known to those skilled in the art (see FIG. 15).

In preparing the apparatus of the invention for use, the controller means is initially programmed in the manner previously described in accordance with instructions from the treating physician. As illustrated in FIGS. 30 and 31, the controller means of this latest form of the invention is substantially identical to that earlier described and comprises the two central processing units and the telemetry assembly 116, a RAM/ROM memory 118, the power supply, or battery 224, feed back electronics, various amplifiers, such as amplifier 110, a circuit interface 122, an antenna coupler 124, a real time clock 126, I/O Bus 128, logic circuits 130, timing and control switch matrix circuits and various related circuitry. Further details concerning the controller means and its relationship with the operating components of the delivery device, including the earlier described sensor means, are also shown in block diagram form in FIG. 31. As before, this figure, like FIG. 16, shows the relative relationship among the previously described fill means of the device, the fluid reservoirs, the device gel reservoirs, the light source, the catheter and the linear displacement measuring means. Additionally, FIG. 31 illustrates, in block diagram form, the relationship among these components and the various components and related systems that make up the electronics of the device that are mounted on the PC boards 156 and 160, including the central processing units, the RAM/ROM memory, the digital signal processor, the logic circuit, and the telemetry assembly.

Upon filling the basal and bolus reservoirs 172 and 208a using the fill means of the invention and after the controller means is initially programmed, the device can be implanted into the patient in the manner shown in FIG. 20. This done, the antenna means and the frequency transmitting means of the invention which are identical to those previously described are used to commence the basal medicament delivery to the patient by energizing light sheet 192.

Figure 24:
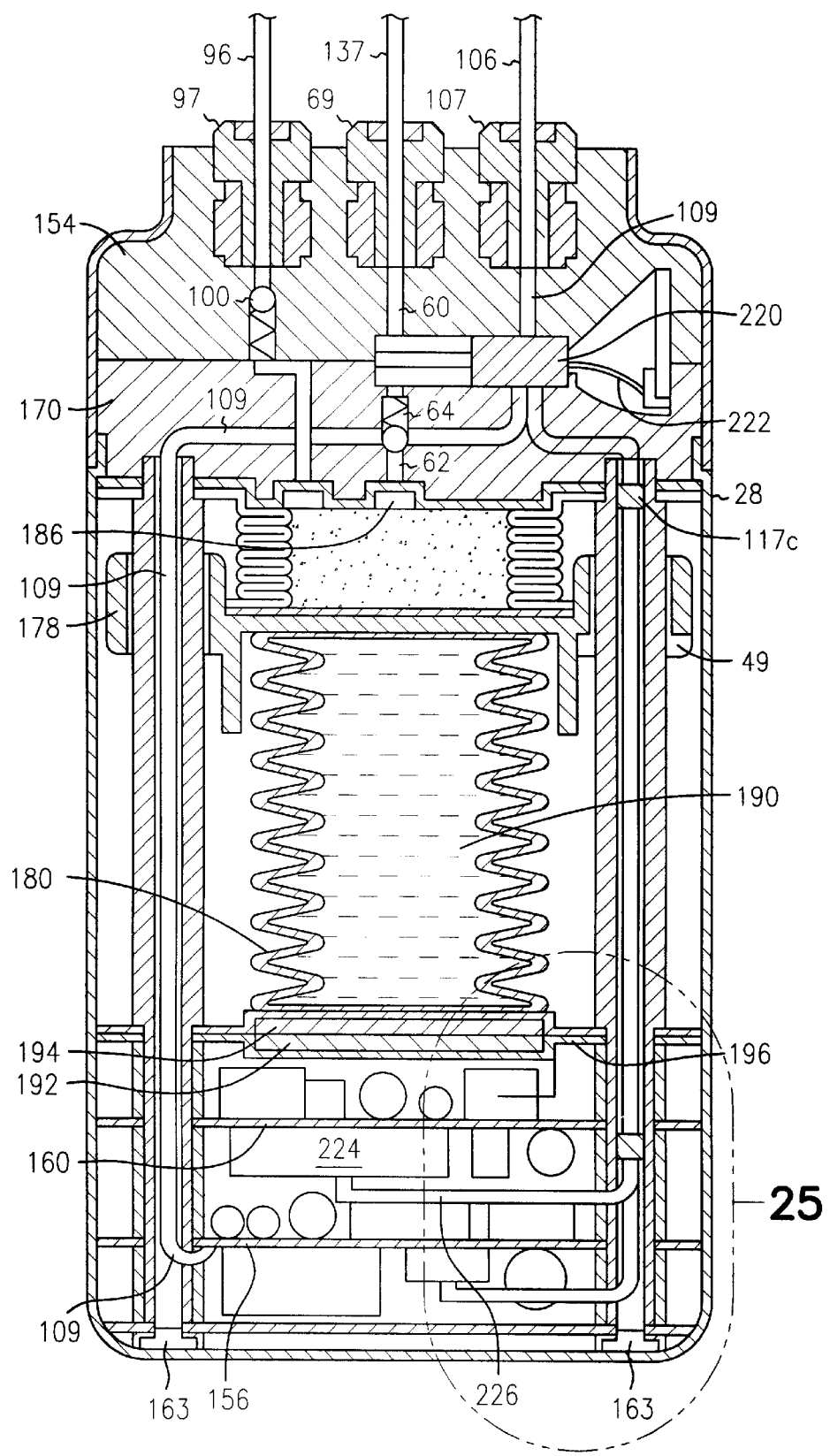
FIG. 24 is a cross-sectional view similar to FIG. 21, but showing the light-activated gel in an expanded configuration following delivery of the medicament to the patient.
Figure 25:
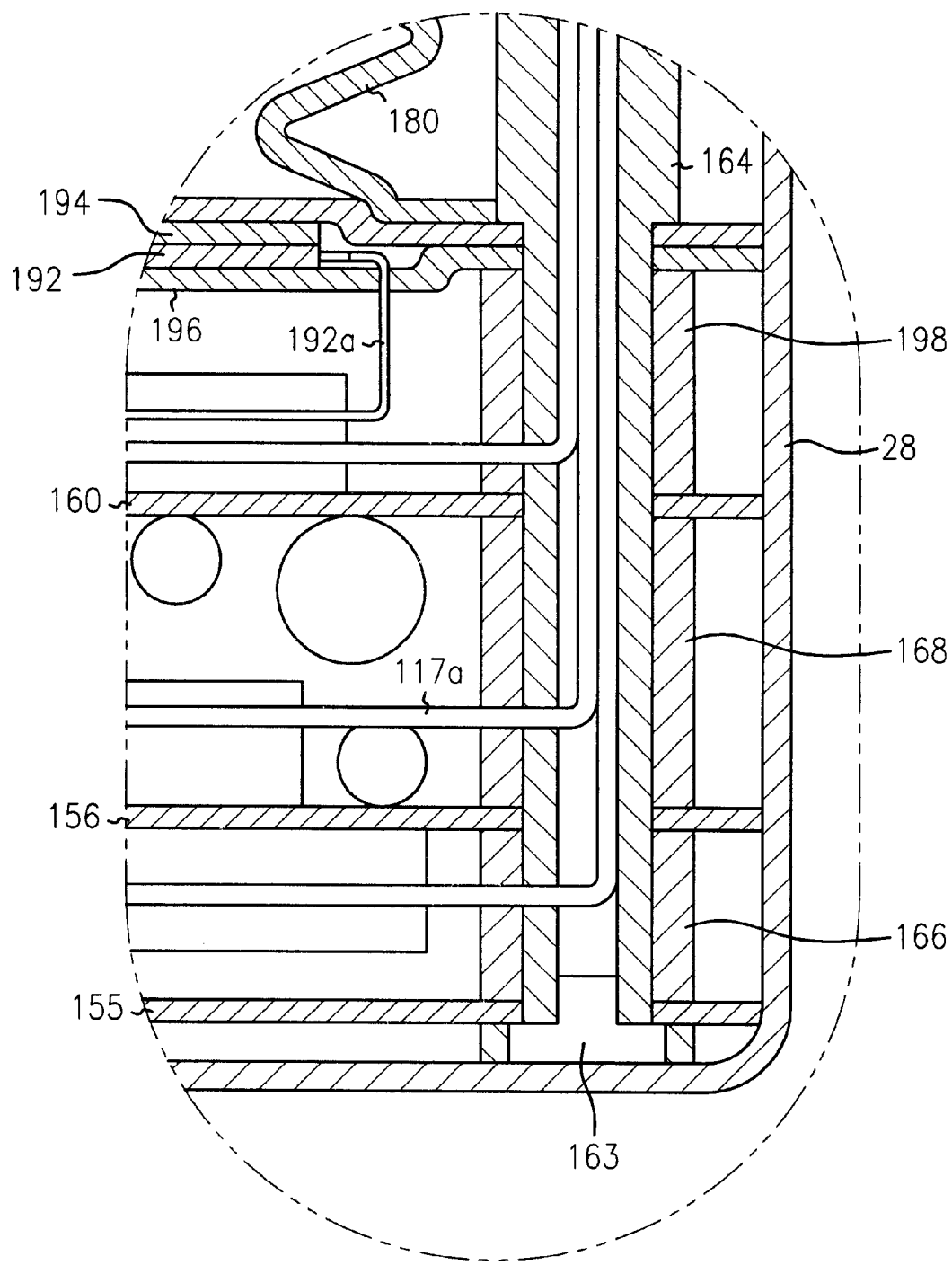
FIG. 25 is an enlarged, cross-sectional view of the area designated as "25" in FIG. 24.

Upon energizing light sheet, the expandable gel 190 will expand into the configuration shown in FIG. 24 causing fluid to be controllably expelled from the device via the infusion means of the invention which is also identical to that previously described.

When it is desired to deliver a bolus dose of medicament to the patient, the antenna means and the frequency transmitting means are used to cause current flow through laminate 210 via leads 214a and 216a and connector block 215 (FIG. 28) which are connected to CPU/Electronic Controllers in the manner shown in FIG. 31. Current flowing through laminate 210 will cause the laminate to bend urging bolus piston 220 inwardly of reservoir 208a thereby causing a bolus dose of fluid to be controllably expelled from the device via cannula 137 of the infusion means of the invention.

By referring once again to FIGS. 17 and 17A it is to be observed that the controller means can be programmed to deliver basal doses to the patient at predetermined volumes and at various intervals R1, R2, and RN as may be desired by the physician. Similarly, by appropriate programming of the controller means, bolus doses of medicament can be delivered to the patient in controlled volumes or quantities at selected frequencies in the manner illustrated in FIG. 17A.

Having now described the invention in detail in accordance with the requirements of the patent statues, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. An implantable device for implantation within a patient for infusing medicinal fluid into the patient comprising:
   (a) a housing having an outlet;
   (b) a first fluid reservoir containing a fluid disposed within said housing, said fluid reservoir having an inlet and an outlet in communication with said outlet of said housing;
   (c) a first mass disposed within said housing proximate said first reservoir, said first mass comprising a semi-solid, which upon being stimulated, will act upon said fluid contained within said first reservoir to cause said fluid to flow outwardly of said outlet of said first reservoir;
   (d) first stimulation means for stimulating said first mass, said first stimulation means being operably associated with said first mass;
   (e) infusion means in communication with outlet of said housing for delivering fluid from said fluid reservoir to the patient; and
   (f) bolus delivery means in communication with said infusion means for delivering a bolus dose of medicinal fluid to said patient.

2. The device as defined in claim 1 further including linear displacement measuring means disposed within said housing for determining the volume of fluid within said first fluid reservoir.

3. The device as defined in claim 1 in which said bolus delivery means comprises:
   (a) a second reservoir disposed within said housing and containing a fluid, said second reservoir having an inlet and an outlet in communication with said outlet of said housing;
   (b) a second mass disposed within said housing proximate said second reservoir, which upon being stimulated, will act upon said fluid contained within said second reservoir to cause said fluid to flow outwardly of said outlet of said second reservoir; and
   (c) second stimulation means operably associated with said second mass for stimulating said second mass.

4. The device as defined in claim 3 in which said second mass is contained within an expandable structure disposed within said housing.

5. The device as defined in claim 3 in which said first mass comprises a thermo-responsive gel.

6. The device as defined in claim 3 in which said second mass comprises a magnetically stimulated gel.

7. The device as defined in claim 3 in which said second mass comprises an electro-responsive gel.

8. The device as defined in claim 3 further including infusion means connected to said housing and communicating with said first reservoir for delivering fluid from said first reservoir to the patient.

9. The device as defined in claim 3 in which said second reservoir is in communication with said first reservoir.

10. The device as defined in claim 3 further including linear displacement measurement means carried within said housing for measuring the volume of a fluid within said first fluid reservoir.

11. The device as defined in claim 3 further including fill means in communication with said first reservoir for filling said first reservoir.

12. The device as defined in claim 11 in which said fill means comprises a fill line and a remote fill septum in communication with said inlet of said first fluid reservoir, said septum being pierceable by a cannula inserted into said septum.

13. The device as defined in claim 11 further including sensor means connected to said housing for sensing physiological changes in the patient.

14. An implantable device for implantation within a patient for infusing medicinal fluid into the patient comprising:

(a) a housing having an outlet;

(b) a first fluid reservoir containing a fluid disposed within said housing, said first fluid reservoir having an inlet and an outlet in communication with said outlet of said housing;

(c) a first mass disposed within said housing proximate said first reservoir, said first mass comprising a semi-solid, which upon being stimulated, will act upon said fluid contained within said first reservoir to cause said fluid to flow outwardly of said outlet of said first reservoir;

(d) first stimulation means operably associated with said first mass for stimulating said first mass;

(e) a second reservoir containing fluid disposed within said housing, said second reservoir having an inlet and an outlet in communication with said outlet of said housing;

(f) a second mass disposed within said housing proximate said second reservoir, which upon being stimulated, will act upon said fluid contained within said second reservoir to cause said fluid to flow outwardly of said outlet of said second reservoir; and (g) second stimulation means operably associated with said second mass for stimulating said second mass.

15. The device as defined in claim 14 in which said first mass is disposed within an expandable structure disposed within said housing.

16. The device as defined in claim 14 in which said first mass comprises a thermo-responsive gel.

17. The device as defined in claim 14 in which said first mass comprises a light stimulated gel.

18. The device as defined in claim 14 in which said second mass comprises a magnetically stimulated gel.

19. The device as defined in claim 14 in which said second mass comprises an electro-responsive polymer.

20. The device as defined in claim 14 further including linear displacement measuring means carried within said housing for determining the volume of fluid within said first fluid reservoir.

21. The device as defined in claim 14 further including infusion means connected to said housing for infusing medicinal fluid into the patient, said infusion means comprising a cannula connected to said outlet of said housing.

22. The device as defined in claim 14 in which said second reservoir is in communication with said first reservoir.

23. The device as defined in claim 14 further including sensor means connected to said housing for detecting physiochemical changes in the patient's body.

24. The device as defined in claim 14 in which said second mass comprises a laminate gel construction.

25. The device as defined in claim 14 in which said second mass comprises a solid polymeric electrolyte disposed between two electrically conducting polymers.

26. The device as defined in claim 14 further including fill means in communication with said first reservoir for filling said first reservoir.

27. The device as defined in claim 26 in which said fill means comprises a fill line and a fill septum in communication with said inlet of said first fluid reservoir, said septum being pierceable by a cannula inserted into said septum.

28. An implantable device for implantation within a patient for infusing medicinal fluid into the patient comprising:

(a) a housing having an outlet;

(b) a first fluid reservoir containing a fluid disposed within said housing and containing a fluid, said fluid reservoir comprising an expandable structure having an inlet and an outlet in communication with said outlet of said housing;

(c) a first mass disposed within said housing proximate said first reservoir, said first mass comprising a polymer gel, which upon being stimulated, will act upon said fluid contained within said first reservoir to cause said fluid to flow outwardly of said outlet of said first reservoir;

(d) first stimulation means for stimulating said first mass, said first stimulation means being operably associated with said first mass;

(e) infusion means in communication with outlet of said housing for delivering fluid from said fluid reservoir to the patient;

(f) bolus delivery means in communication with said infusion means for delivering a bolus dose of medicinal fluid to said patient; and (g) linear displacement measuring means disposed within said housing for determining the volume of fluid within said first fluid reservoir.

29. The device as defined in claim 28 in which said linear displacement measuring means comprises a magnet and an operably associated waveguide disposed within said housing.

30. The device as defined in claim 28 in which said linear displacement measuring means comprises magnetostrictive sensor.

31. The device as defined in claim 28 further including fill means in communication with said first reservoir for filling said reservoir.

32. The device as defined in claim 31 in which said fill means comprises a fill line and a fill septum in communication with said inlet of said first fluid reservoir, said septum being pierceable by a cannula inserted into said septum.

33. The device as defined in claim 32 further including sensor means connected to said housing for sensing physiological changes in the patient.

\* \* \* \* \*